(12) United States Patent
Carnal et al.

(10) Patent No.: US 7,406,874 B2
(45) Date of Patent: Aug. 5, 2008

(54) CORROSION FUSE

(75) Inventors: Steven E. Carnal, Milan, TN (US); Lew Tobias, Washington Township, MI (US)

(73) Assignee: Black & Decker Inc., Newark, DE (US)

( * ) Notice: Subject to any disclaimer, the term of this patent is extended or adjusted under 35 U.S.C. 154(b) by 0 days.

(21) Appl. No.: 10/914,509

(22) Filed: Aug. 9, 2004

(65) Prior Publication Data

US 2006/0101920 A1    May 18, 2006

Related U.S. Application Data

(60) Provisional application No. 60/565,914, filed on Apr. 28, 2004.

(51) Int. Cl.
*G01L 7/00* (2006.01)
(52) U.S. Cl. .................................................. 73/706
(58) Field of Classification Search .................... 73/706
See application file for complete search history.

(56) References Cited

U.S. PATENT DOCUMENTS

| | | | |
|---|---|---|---|
| 629,092 A | 7/1899 | Ross | |
| 2,339,303 A | 1/1944 | Tillery | 220/1 |
| 2,343,440 A | 3/1944 | Andrus | 204/197 |
| 2,356,957 A | 8/1944 | Turner | 27/35 |
| 2,380,964 A | 8/1945 | Grover | 220/89 |
| 2,786,643 A | 3/1957 | Carlstedt | 251/144 |
| 3,367,623 A | 2/1968 | Piel | 251/144 |
| 3,423,305 A | 1/1969 | Tausk | 204/197 |
| 3,867,274 A | 2/1975 | Herman | 204/197 |
| 3,978,309 A | 8/1976 | Strobach et al. | 219/104 |
| 4,013,811 A | 3/1977 | Maruska | 428/35 |
| 4,051,007 A | 9/1977 | Hössle | 204/197 |
| 4,087,742 A * | 5/1978 | Khoo | 205/731 |
| 4,093,529 A | 6/1978 | Strobach | 204/197 |
| 4,136,001 A | 1/1979 | Nozaki | 204/196 |
| 4,146,448 A | 3/1979 | Nakano et al. | 204/148 |
| 4,333,516 A | 6/1982 | Krueger et al. | 165/1 |
| 4,347,942 A | 9/1982 | Jernberg et al. | 220/89 A |
| 4,602,652 A | 7/1986 | Ayers | 137/15 |
| 4,654,191 A | 3/1987 | Krieg | 376/283 |
| 4,738,372 A | 4/1988 | Jernberg | 220/89 A |

(Continued)

FOREIGN PATENT DOCUMENTS

JP          2000019098 A    *   1/2000

*Primary Examiner*—Max Noori
(74) *Attorney, Agent, or Firm*—Michael P. Leary; Adan Ayala

(57) ABSTRACT

A corrosion fuse is a device connected with a compressed air tank in order to provide a predictive indication of corrosive activity occurring within the compressed air tank. The corrosion fuse includes a corrosion detector established as a thin-walled metal tube closed on one end and open to an environment outside the compressed air tank on the other end. The joining of the corrosion fuse with the compressed air tank is enabled by the connection of a plug with a fitting (i.e., flange). The plug connects to the open end of the corrosion detector and with the flange. The flange is connected to the compressed air tank about a tank receiver disposed on the compressed air tank. The tank receiver allows the corrosion detector, connected with the plug, to at least partially extend inside the compressed air tank, when the plug is connected with the flange.

19 Claims, 22 Drawing Sheets

U.S. PATENT DOCUMENTS

| | | | |
|---|---|---|---|
| 4,846,363 A | 7/1989 | Gough | 220/3 |
| 4,848,616 A | 7/1989 | Nozaki | 219/322 |
| 4,907,617 A | 3/1990 | Whalen | 137/71 |
| 4,930,648 A | 6/1990 | Hundt | 220/1 B |
| 5,023,928 A | 6/1991 | Houle et al. | 392/457 |
| 5,067,690 A | 11/1991 | Bac | 251/149.8 |
| 5,144,973 A | 9/1992 | Green et al. | 137/71 |
| 5,217,202 A | 6/1993 | Phillips | 251/144 |
| 5,256,267 A | 10/1993 | Roden | 204/196 |
| 5,334,299 A | 8/1994 | Roden | 204/196 |
| 5,433,410 A | 7/1995 | Foltz | 251/100 |
| 5,503,295 A | 4/1996 | Kotarba et al. | 220/581 |
| 5,518,032 A | 5/1996 | Berke | 137/899.4 |
| 6,233,958 B1 | 5/2001 | Mei et al. | 62/238.7 |
| 6,367,328 B1* | 4/2002 | Gorman et al. | 73/592 |
| 6,742,995 B1* | 6/2004 | Wood et al. | 417/234 |
| 6,770,177 B2 | 8/2004 | Keller et al. | 204/196.37 |
| 6,809,506 B2* | 10/2004 | Thomas et al. | 324/71.1 |
| 6,896,779 B2* | 5/2005 | Thomas et al. | 204/404 |
| 6,902,661 B2* | 6/2005 | Thomas et al. | 205/776.5 |
| 6,923,627 B1* | 8/2005 | Wood et al. | 417/234 |
| 2004/0047745 A1* | 3/2004 | Burkholder et al. | 417/234 |
| 2004/0197200 A1* | 10/2004 | Wood et al. | 417/234 |
| 2004/0258846 A1* | 12/2004 | Vaerewyck et al. | 427/430.1 |
| 2005/0006251 A1* | 1/2005 | Thomas et al. | 205/725 |

* cited by examiner

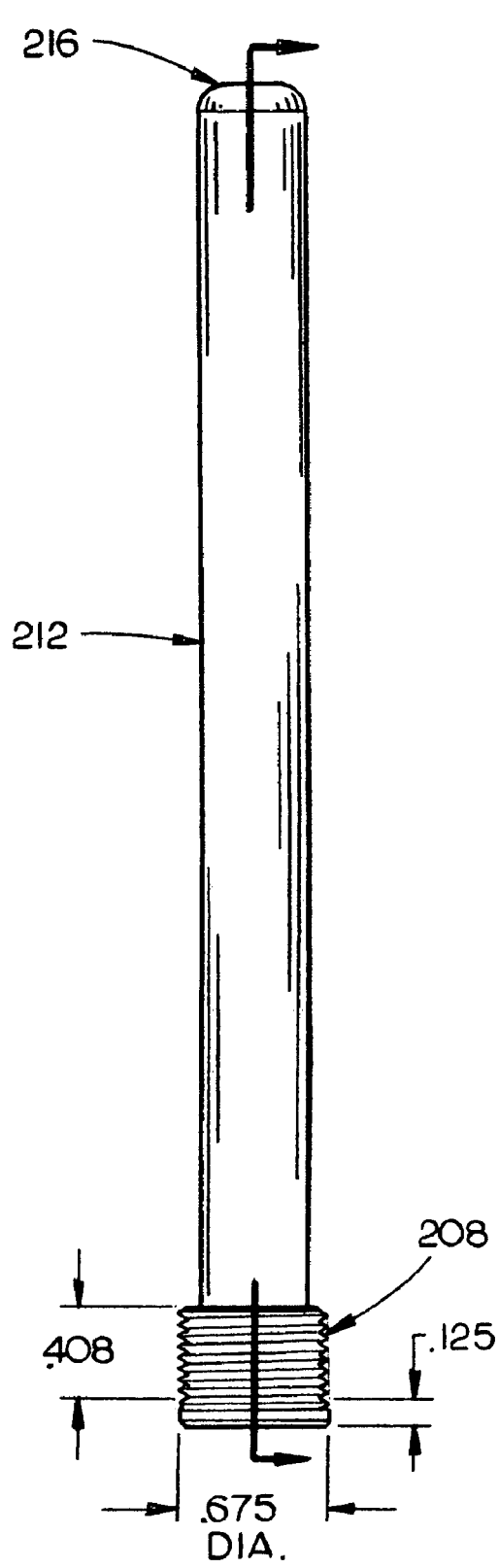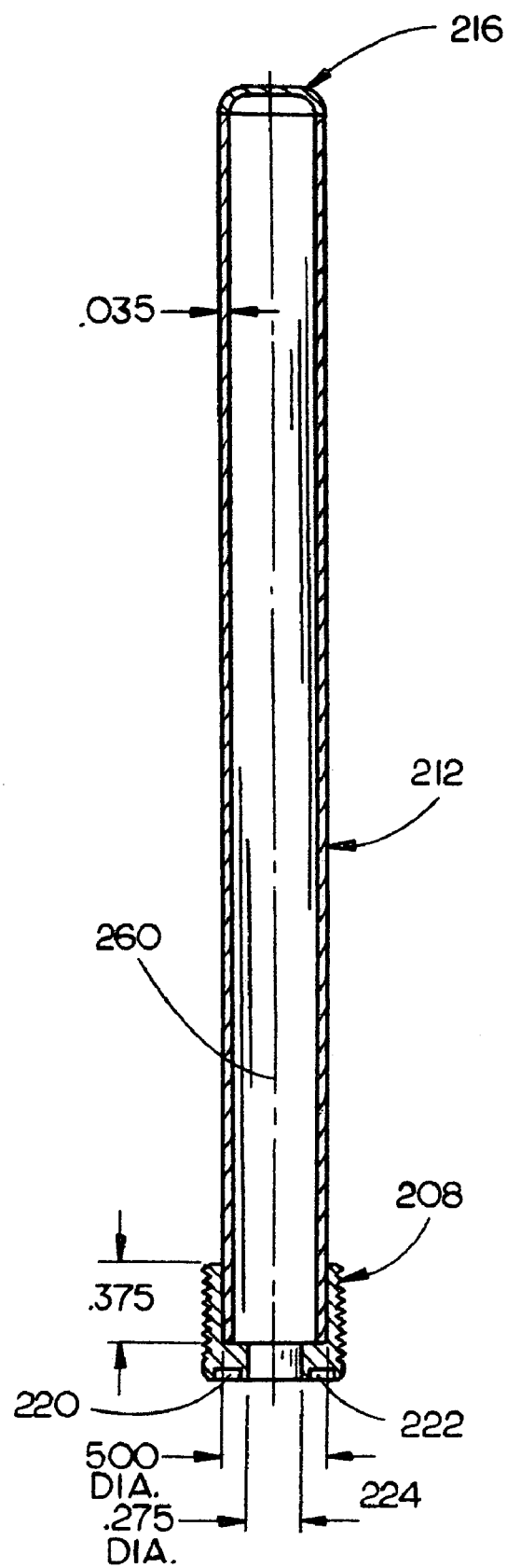

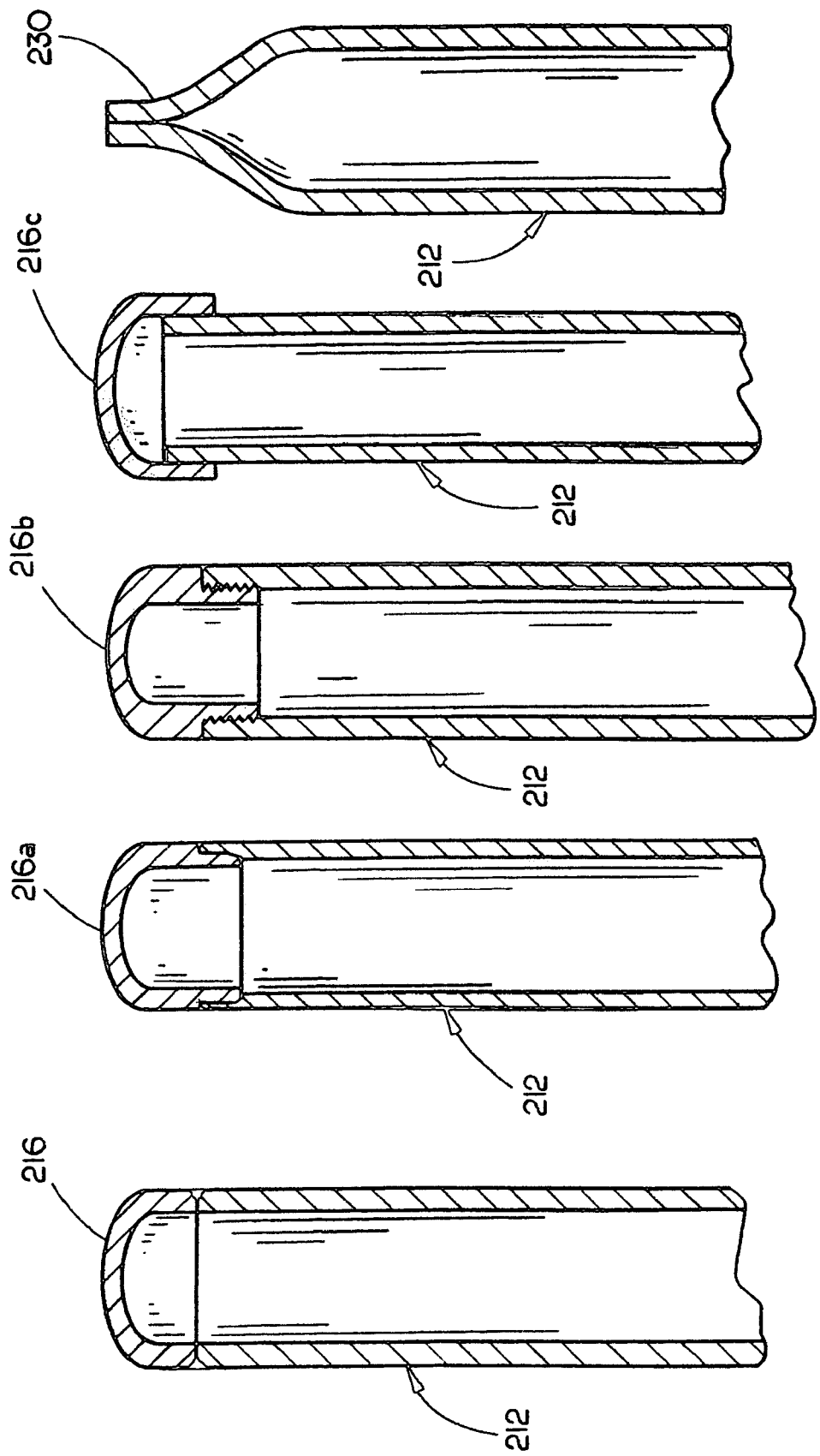

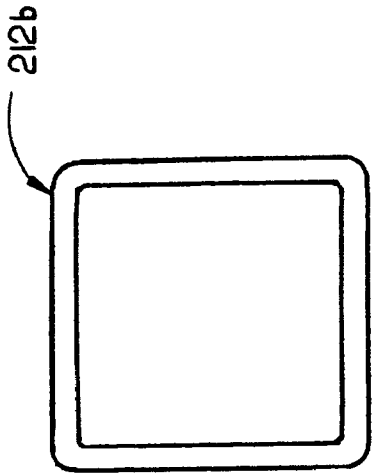
FIG. 15
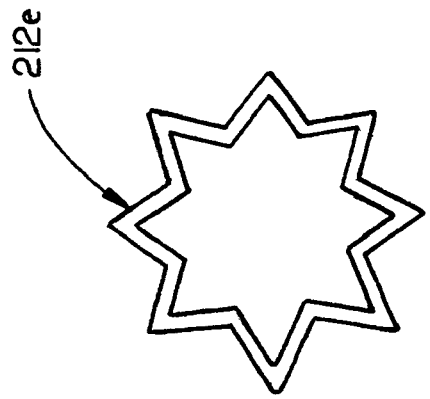
FIG. 18
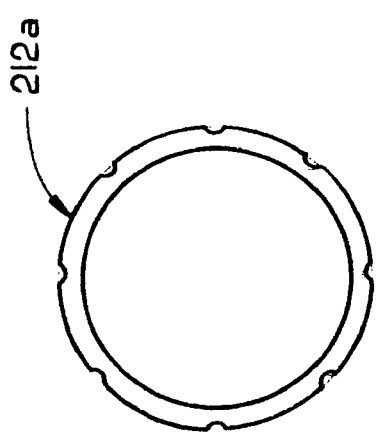
FIG. 14
FIG. 17
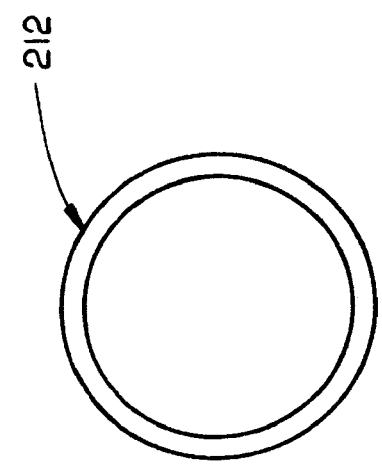
FIG. 13
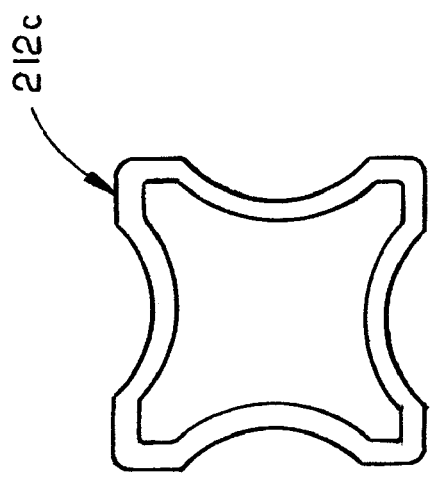
FIG. 16

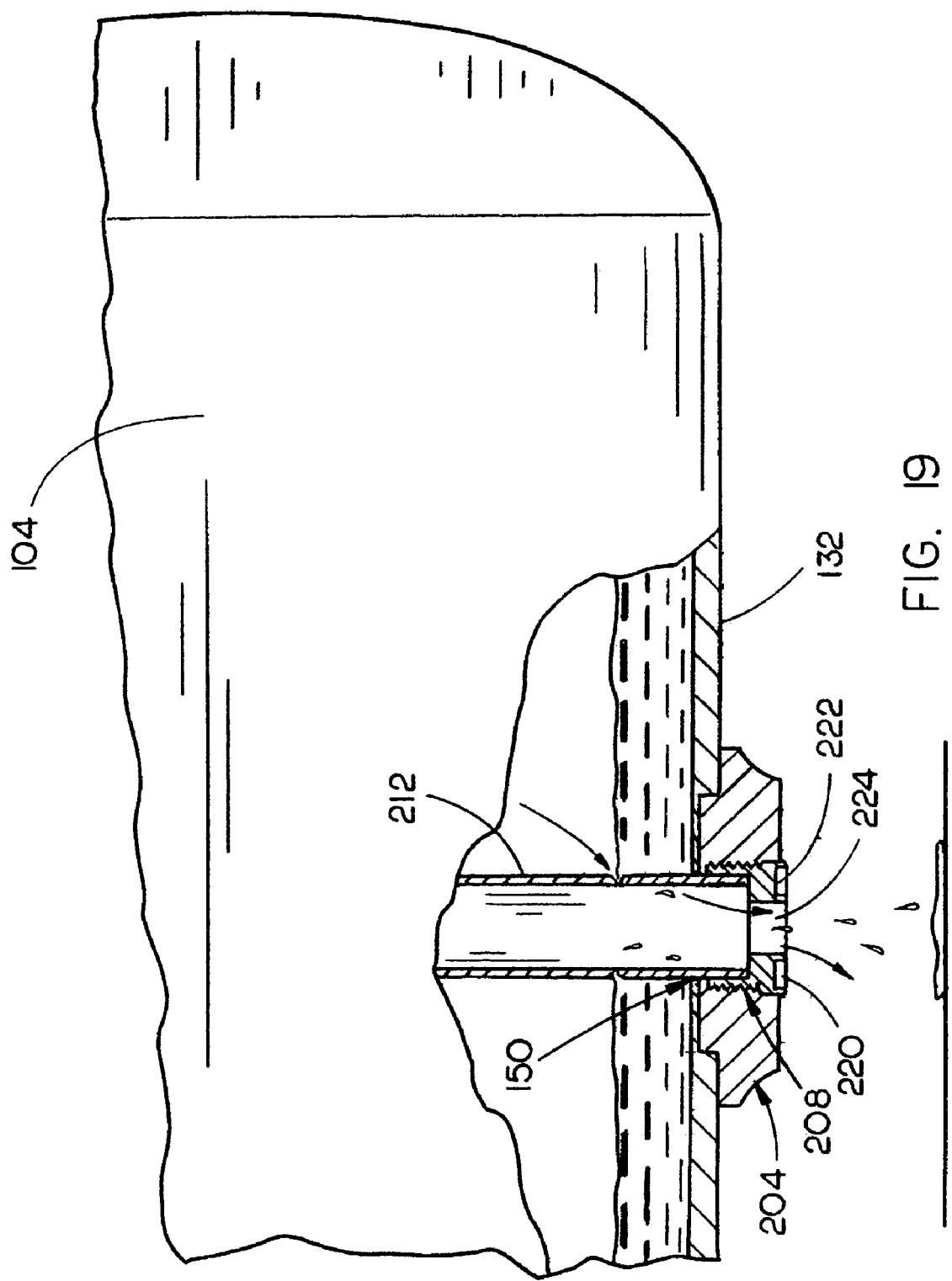

CORROSION FUSE

CROSS REFERENCE TO RELATED APPLICATION

The present invention claims priority under 35 U.S.C. §119 (e) to the U.S. Provisional Patent Application Ser. No. 60/565,914, filed on Apr. 28, 2004, which is herein incorporated by reference in its entirety.

FIELD OF THE INVENTION

The present invention generally relates to the field of compressed air storage containers, such as air tanks utilized in air compressors, and particularly to an apparatus for providing a predictive indication of corrosive activity occurring within the air tanks.

BACKGROUND OF THE INVENTION

Compressed air storage containers/pressure vessels/air tanks are employed for the storage of air at elevated pressures. These air tanks are widely employed to enable the functionality of various mechanisms, such as pressure washers and air driven tools, and may commonly be utilized in the consumer market, residing in consumer's shops, garages, and barns. A typical problem associated with the use of these compressed air tanks is that due to humidity in the air and temperature changes moisture (i.e., water) may build up within the tank which may lead to corrosion of the tank, if the tank is not properly maintained by regularly draining the condensate from the tank. Compressed air tanks commonly include drain plugs which allow the operator to perform proper maintenance draining. However, it may be the case that operators may fail to properly maintain the air tanks, thereby, resulting in an amount of condensate residing in the air tank for an extended period of time. This water may lead to corrosion of the inside of the air tank with no indication of damage viewing the air tank from the outside. The corrosion of the air tank may lead to a rupture of the tank walls, which may result in a decreased useful life span and serious damage to the air tank.

Compressed air tanks may be composed of various materials. Steel is often employed in the construction of these air tanks. Steel corrosion by water is typically described by a single corrosion rate, usually millimeters (or thousandths of an inch) per year. This corrosion is generally thought to be uniform (i.e., the same at all points on the corroding surfaces.) However, steel corrosion is often not uniform and may have pits or other localized corrosion.

For pitting corrosion, the corrosion rate is measured at the maximum pit depth and the rate can be as high as three times the uniform corrosion rate for the same material under the same environmental conditions. Severe pitting may lead to a leak while some structural strength remains. Thus, for a corroding compressed air tank of an air compressor, pitting may lead to leaks before a rupture may occur. This is referred to as "leak-before-burst".

Another form of non-uniform corrosion is known as "waterline attack". In this corrosion process, the corrosion rate is greater at the splash zone or the intersection of the metal, the corroding liquid, and air. This may result in a "line", commonly referred to as a "waterline" in the air tank that is a thinner or weaker section of the air tank than the surrounding area. A waterline, long length of thin metal, aligned perpendicular to the maximum stress direction, the hoop stress direction, may result in a rupture well before an expected rupture based on metal thickness in the area of uniform corrosion.

Compressed air tanks are typically assembled from formed flat sheets of steel that are welded together. The welding process alters the local metal structure in and near the weld, establishing a fusion region. This may lead to non-uniform corrosion of the metal in or near the fusion region. The fusion region of the weld (metal that was molten) has more microstructure variation than wrought metal and may be prone to pitting. There is a region near the weld that does not melt, but gets hot enough to alter the metallurgical structure. This is called the heat-affected zone (HAZ). This different metallurgical structure may cause local corrosion attack. If local corrosion occurs at the HAZ it may be manifested as a line of thin metal next to the weld. Like waterline attack, localized corrosion in the HAZ may lead to a rupture before one is predicted using expected metal thickness estimated from uniform corrosion.

Currently, many available compressed air tanks employ a method commonly referred to as a "telltale hole" for assisting an operator in identifying internal tank corrosion. This method typically entails mechanically thinning the wall of the tank with a single, small diameter "telltale hole". The telltale hole partially penetrates the wall of the tank. The partial penetration hole established is cut from the outside and when the remaining metal of the tank wall corrodes away, the tank leaks at the hole to warn that the tank's useful life has expired. Unfortunately, this method assumes that the first place a tank will leak due to corrosion will be at the "telltale hole" and that when a leak occurs at the "telltale hole", rupture of the tank will generally be averted because there is still enough metal surrounding the hole and in the rest of the tank to support the pressure and avoid rupture or bursting.

The problem with this method is that the location for drilling the "telltale hole" is typically at the bottom of the tank and may not accurately reflect the degree of corrosion that is occurring further up the wall of the tank, from the bottom of the tank up to and including the "waterline" and above. The "waterline" being the point of intersection of the metal of the tank, corroding liquid within the tank, and remaining air within the tank. This may be problematic because there are occasions where the corrosion rate may be much greater at various locations up the tank wall, such as at the "waterline", than at the point where the "telltale hole" is drilled. When the rate of corrosion is greater at the "waterline", this is commonly referred to as "waterline attack" as stated previously, and may result in a catastrophic rupture of the tank at the "waterline", well before a leak occurs at the "telltale hole".

Therefore, it would be desirable to provide an apparatus enabled to detect corrosive effects occurring within a compressed air tank at various locations within the compressed air tank.

SUMMARY OF THE INVENTION

It is an object of the present invention to provide a device which is intended to corrosively fail before the compressed air tank fails from corrosion. The present invention is intended to work alone or in conjunction with various mechanical components of compressed air tanks, such as a tank drain valve and manifold, which promote the proper operation of the compressed air tank. Accordingly, in a first aspect of the present invention, a corrosion fuse is provided. The corrosion fuse includes a corrosion detector connected with a plug. The corrosion detector is intended to be at least partially disposed within a compressed air tank and assists in providing a predictive indication of corrosive activity occurring within the compressed air tank. The plug assists in connecting the corrosion detector with the compressed air tank.

The plug may connect directly with the compressed air tank or via a fitting which is connected with the compressed air tank.

In a second aspect of the present invention, a corrosion fuse is connected with a compressed air tank in order to assist in protecting the compressed air tank from experiencing a catastrophic failure caused by the corrosive action of internal moisture. In a preferred embodiment, the corrosion fuse includes a corrosion detector established as a thin-walled metal tube closed on one end and open on the other. The open end may be joined to the compressed air tank in a variety of locations. The joining of the corrosion fuse with the compressed air tank is enabled by a plug connected to the open end of the corrosion detector which may be further coupled with a fitting connected to the compressed air tank about a tank receiver disposed on the air tank. In a preferred embodiment, the fitting is welded to the bottom of the compressed air tank. The closed end of the corrosion detector protrudes into the compressed air tank to provide an indication of corrosion occurring within the air tank. Upon corrosive failure of the corrosion detector, air and additional substances, such as flakes of material from the inside of the compressed air tank, may flow out of the corrosion detector to the outside environment where they may provide evidence to a user that the corrosion detector has failed.

It is an object of the present invention to provide a device which enables the identification of corrosive failure at various locations within a compressed air tank. Thus, the present invention may assist the operator of the compressed air tank in early detection of corrosive failure due to uniform corrosion or non-uniform corrosion, such as pitting corrosion, waterline attack, and the like. An additional object of the present invention is to provide for the determining of corrosive failure rates in variously sized compressed air tanks.

In an alternative aspect of the present invention, a corrosion detection system may be established in conjunction with a compressed air tank. The corrosion detection system includes two or more corrosion fuses coupled with the compressed air tank. It is further contemplated that the corrosion detection system may include an indication assembly which provides an indicator ascertainable by an operator for identifying to the operator the status of the compressed air tank with respect to corrosive failure.

In an additional aspect, the present invention provides a method for detecting the internal corrosive failure rate of a compressed air tank. It is contemplated that this method employs one or more corrosion fuses coupled with the compressed air tank to provide indication of corrosive failure. It is an object of the method to identify the corrosive failure rate at a point in time prior to a rupture of the compressed air tank. It is understood that the method of the present invention may employ the corrosion detection system, as previously identified. In a further aspect of the present invention, a method of manufacturing a compressed air tank including the corrosion fuse is provided. The compressed air tank being formed from the same material as that of the corrosion fuse. Still further, the present invention provides a method of manufacturing an air compressor assembly including a corrosion fuse. The corrosion fuse is connected with a compressed air tank of the air compressor assembly in a manner which enables the corrosion fuse to provide an indication to a user of the air compressor assembly of the corrosive failure rate within the air tank.

It is to be understood that both the foregoing general description and the following detailed description are exemplary and explanatory only and are not restrictive of the invention. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which:

FIG. 4 is a side view of the corrosion fuse in accordance with the present invention;

FIG. 5 is a cross-sectional view illustrating the corrosion fuse in accordance with the present invention;

FIG. 8 is an expanded cross-sectional view illustrating the connection between a first end of a corrosion detector and a first exemplary cap of the corrosion fuse in accordance with an exemplary embodiment of the present invention;

FIG. 9 is an expanded cross-sectional view illustrating the connection between the first end of the corrosion detector and a second exemplary cap;

FIG. 10 is an expanded cross-sectional view illustrating the connection between the first end of the corrosion detector and a third exemplary cap;

FIG. 11 is an expanded cross-sectional view illustrating the connection between the first end of the corrosion detector and a fourth exemplary cap;

FIG. 12 is an expanded cross-sectional view illustrating the first end of the corrosion detector crimped to provide a sealed first end;

FIG. 13 is a cross-sectional view illustrating a first exemplary configuration of the corrosion detector of the corrosion fuse of the present invention;

FIG. 14 is a cross-sectional view illustrating a second exemplary configuration of the corrosion detector of the corrosion fuse of the present invention;

FIG. 15 is a cross-sectional view illustrating a third exemplary configuration of the corrosion detector of the corrosion fuse of the present invention;

FIG. 16 is a cross-sectional view illustrating a fourth exemplary configuration of the corrosion detector of the corrosion fuse of the present invention;

FIG. 17 is a cross-sectional view illustrating a fifth exemplary configuration of the corrosion detector of the corrosion fuse of the present invention;

FIG. 18 is a cross-sectional view illustrating a sixth exemplary configuration of the corrosion detector of the corrosion fuse of the present invention;

FIG. 19 is a cut-away sectional view illustrating the corrosion fuse indicating corrosive failure of the corrosion detector by the leaking of fluid and release of compressed air from within the compressed air tank;

DETAILED DESCRIPTION OF THE INVENTION

Reference will now be made in detail to the presently preferred embodiments of the invention, examples of which are illustrated in the accompanying drawings.

Referring generally now to FIGS. 1 through 23, exemplary embodiments of the present invention are shown.

Figure 1:
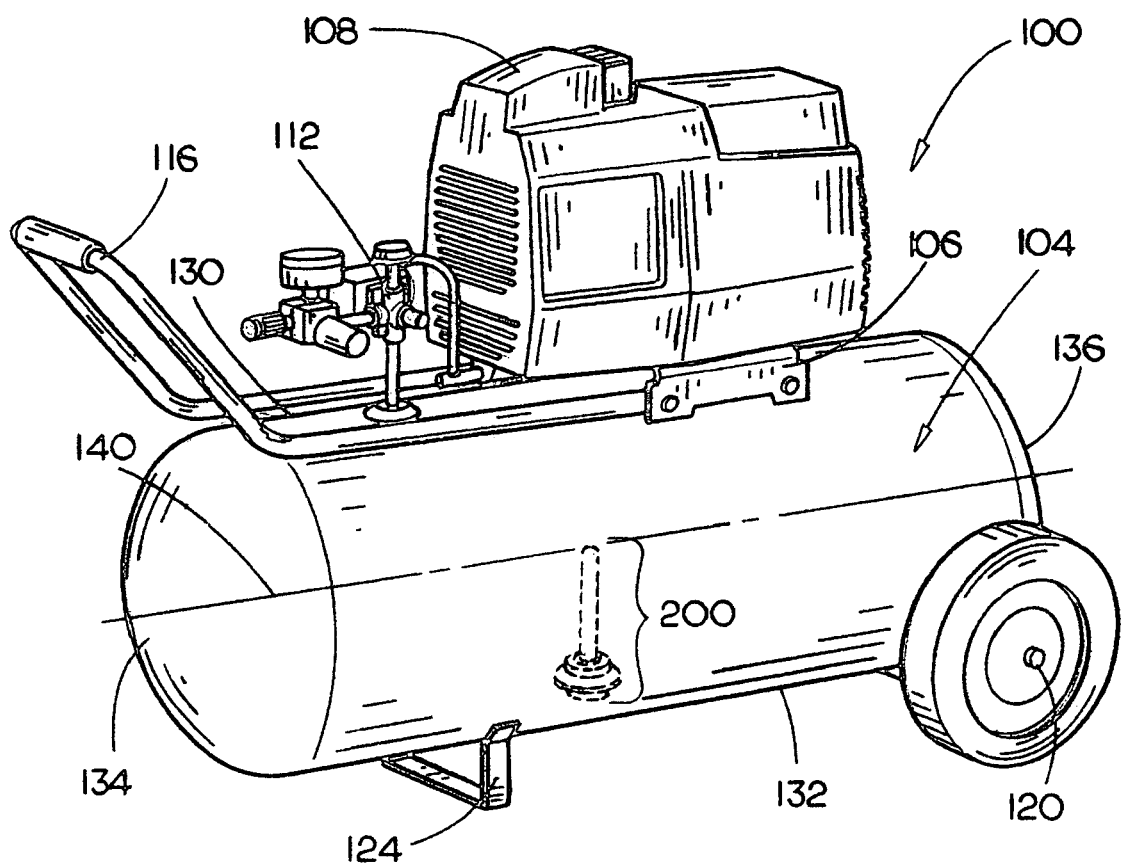
FIG. 1 is an illustration of a horizontal portable air compressor assembly employing a corrosion fuse in accordance with an exemplary embodiment of the present invention.
Figure 2:
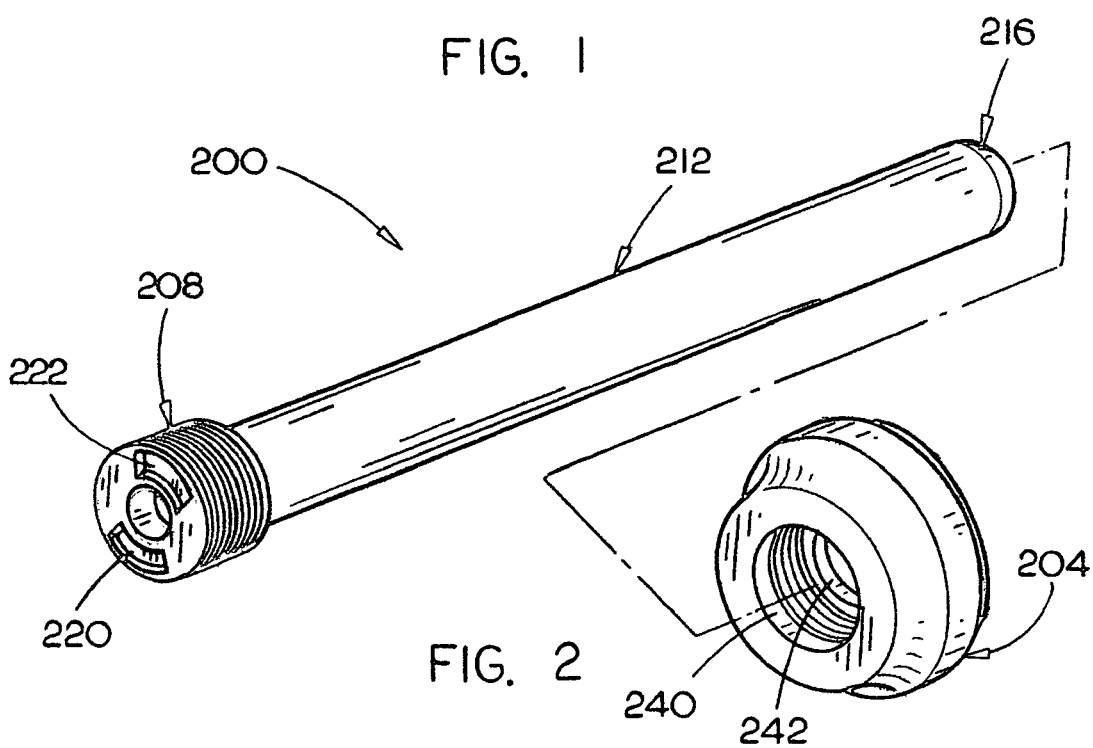
FIG. 2 is an exploded view of the corrosion fuse indicating the connection of a flange with a plug connected with a corrosion detector.
Figure 3:
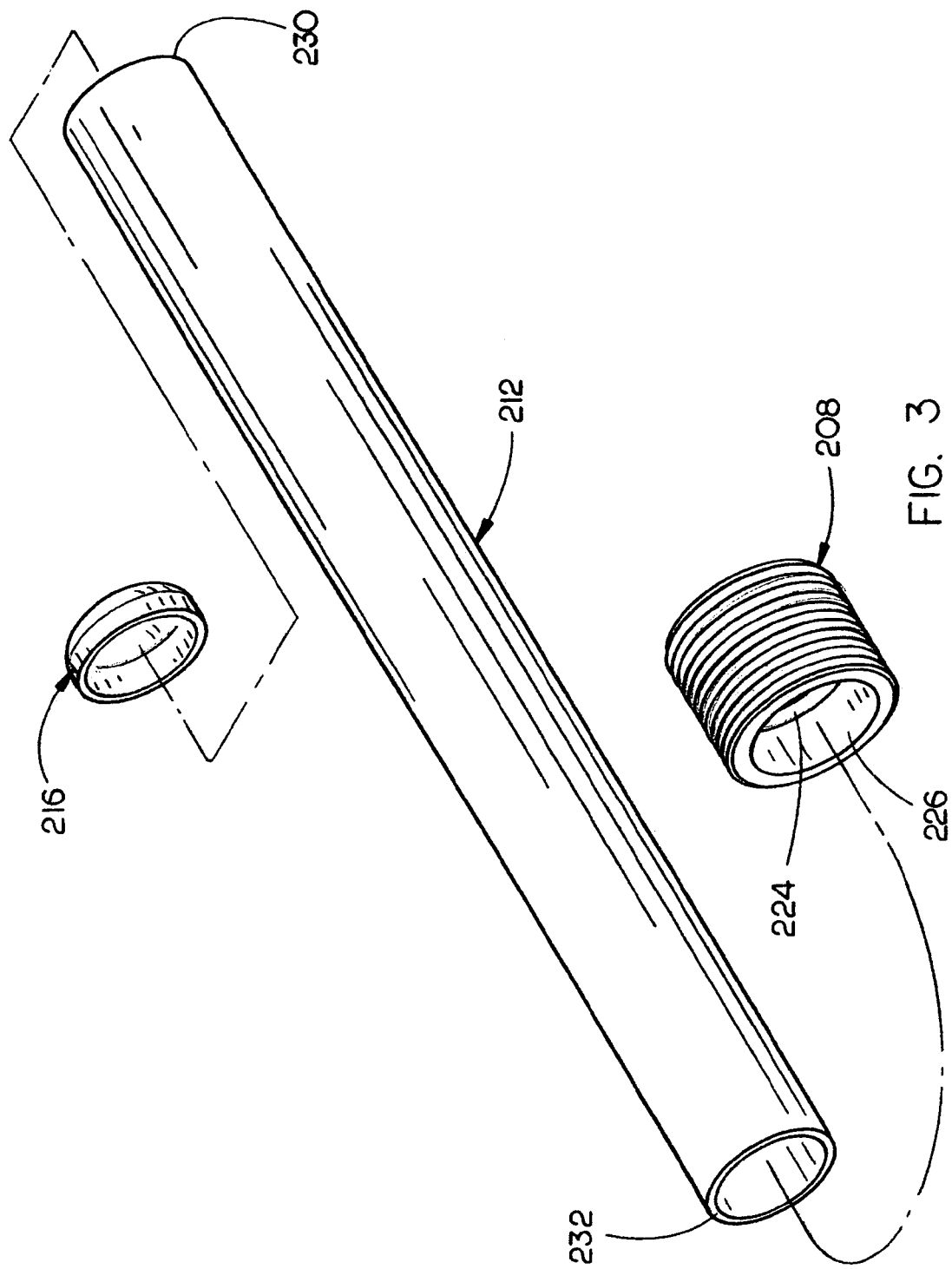
FIG. 3 is an exploded view indicating the connection of the plug with the corrosion detector and the connection of a cap with the corrosion detector.
Figure 6:
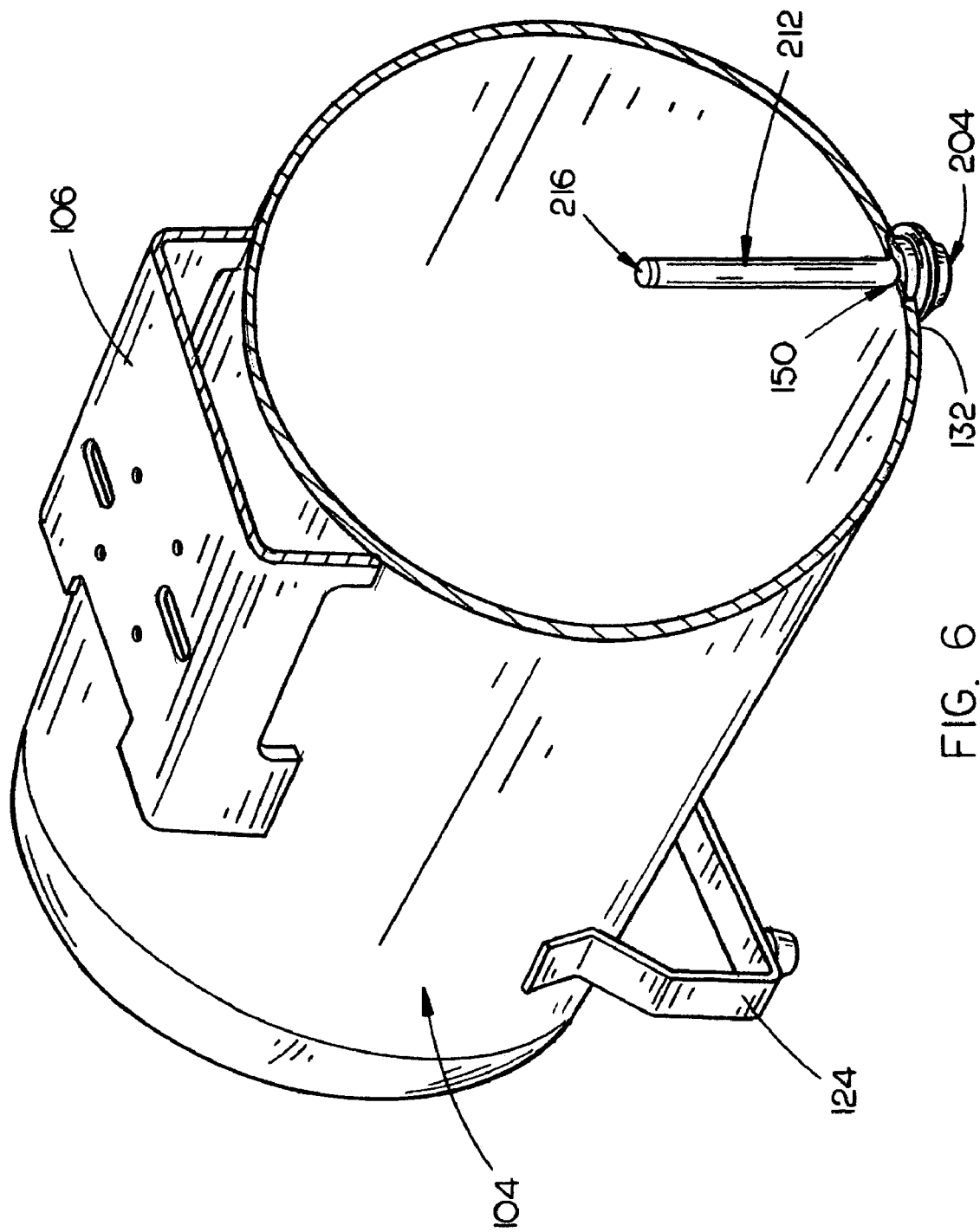
FIG. 6 is a cross-section view illustrating the air compressor assembly including the corrosion fuse.
Figure 7:
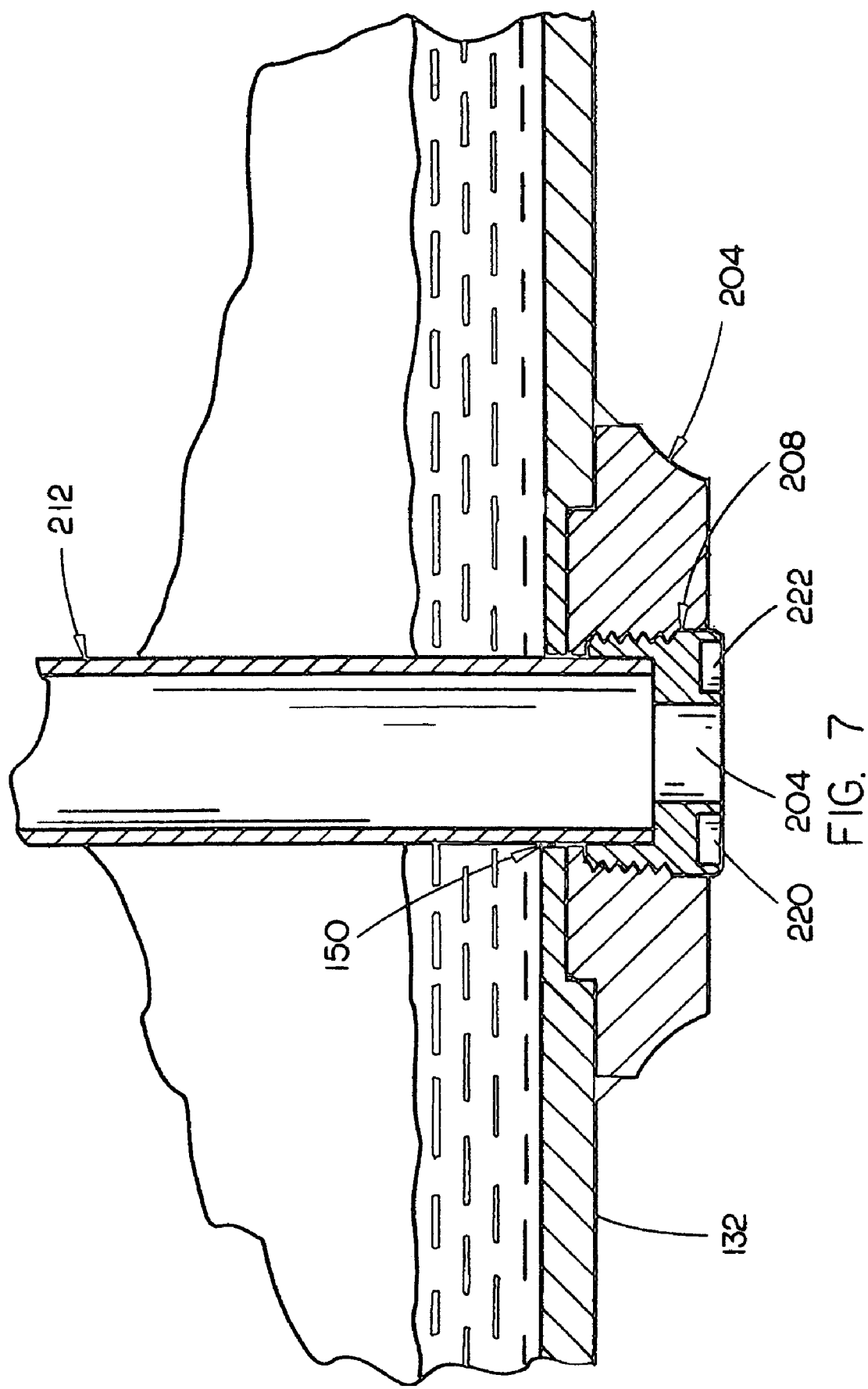
FIG. 7 is an expanded cross-sectional view illustrating the connection of the corrosion fuse via a tank receiver with the compressed air tank of the air compressor assembly.

An air compressor assembly 100 including a corrosion fuse 200 in accordance with an exemplary embodiment is shown in FIG. 1. The corrosion fuse 200 of the present invention includes a corrosion detector 212, which is configured to couple with a plug 208. In a preferred embodiment, the corrosion detector 212 is generally configured as an enclosure, the enclosure being a length of metal tubing, having an axis 270, which is the corrosion detector centerline. Further, the corrosion detector 212 includes a first end 230 and a second end 232. The first end 230 is a first "closed/sealed" end and the second end 232 is open to the outside environment. Thus, the corrosion detector 212 defines an inner recess or inner chamber which is open to the outside environment. The first end 230 may be established as the "closed/sealed" end in a variety of manners. Additionally, the second end 232 is established to provide for coupling with the plug 208.

In a preferred embodiment, a cap 216 is coupled with the first end 230 of the corrosion detector 212. The cap 216 is connected with the first end 230 through use of an adhesive, such as wicking cement adhesive, which securely affixes the position of the cap 216 relative to the first end 230. Further, the wicking cement adhesive may assist in avoiding the penetration of corrosive materials, such as air and/or moisture, within the joint between the cap 216 and the first end 230.

Figure 23:
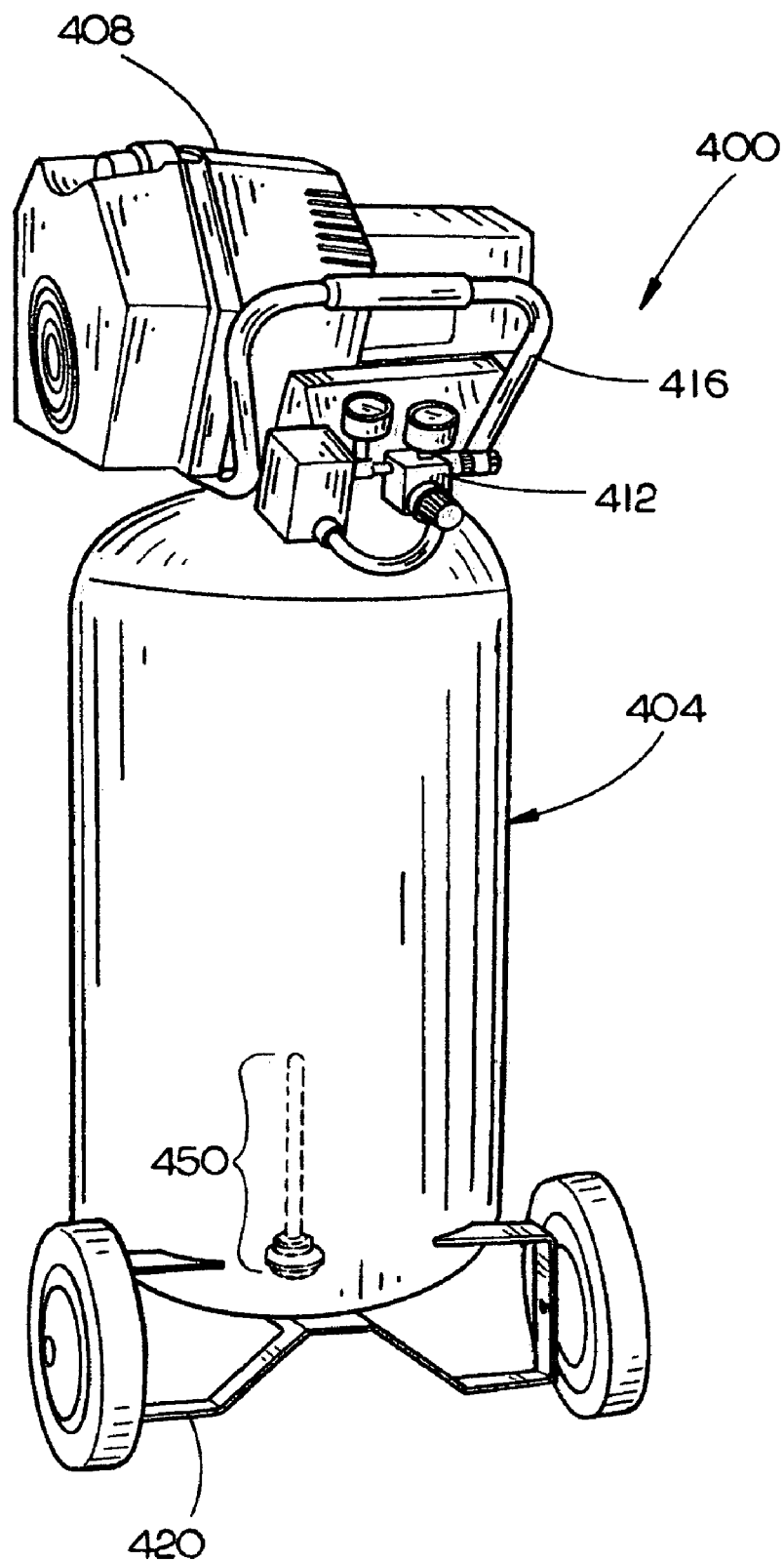
FIG. 23 illustrates an exemplary air compressor assembly employing a corrosion fuse within a vertical compressed air tank in accordance with the present invention.

In the current embodiment, the air compressor assembly 100 is a horizontal tank air compressor assembly. In alternative embodiments, an air compressor assembly employing a corrosion fuse of the present invention is established as a vertical tank air compressor assembly, as shown in FIG. 23. Further, the exemplary embodiments of the air compressor assembly 100 may be portable air compressor assemblies. The air compressor assembly 100 includes a compressed air tank 104 connected with a manifold 112. Further connected to the compressed air tank 104 are a mounting bracket 106, a support 124, and a wheel assembly 120. The mounting bracket 106 connects with a motor 108, which couples with the manifold 112, and a handle 116. The compressed air tank 104 stores compressed air within. The manifold 112 provides a user of the air compressor assembly 100 the ability to access, monitor, and utilize the compressed air stored within the compressed air tank 104.

Compressed air tanks are constructed to meet ASME (American Society of Mechanical Engineers) codes. The certification standards established by ASME are in place to promote the safe operation of devices, such as compressed air tanks. The compressed air tanks may be made from what is classified as low-carbon steel, such as SA-414 Grade G steel, and meet ASME (American Society of Mechanical Engineers) code. The thickness of the walls of compressed air tanks may be constructed at a minimum thickness in order to meet certification standards for the ASME. Currently, the minimum air tank wall thickness for certification under ASME is one hundred and four thousandths (0.104") of an inch. In the current embodiment, the compressed air tank 104 is composed of a low-carbon steel shell meeting the minimum thickness standard of the ASME. Thicker walls may be desirable for increasing the burst pressure the compressed air tank is able to withstand, which may allow the compressed air tanks to store compressed air at higher and higher pressures. Current industry trends include the manufacturing of tools utilizing compressed air provided at elevated pressures (i.e., 125 psi), when compared to past compressed air driven tools which typically utilized air pressures below 125 psi. The material composition of the compressed air tank 104 may be varied. For example, the compressed air tank 104 may be composed of a composite material, different steel alloys, or alternative metals. It is contemplated that the thickness of the walls of compressed air tanks, such as the compressed air tank 104, may be greater than the minimum ASME code requirements.

Different alloys, of the general SA-414 Grade G steel, may corrode similarly in a specific corroding medium, such as water. The steel shell of the compressed air tank 104 is formed to define an inner diameter. For example, the inner diameter may be twelve (12") inches. It is understood that the size of the inner diameter of the shell of the compressed air tank 104 may vary and that the corrosion fuse 200 of the present invention may be employed with these variously sized tanks. For instance, the inner diameter of the compressed air tank 104 may range from six (6") inches to seventy-two (72") inches. Preferably, the inner diameter may range from ten (10") inches to twenty-four (24") inches. The steel shell includes an inner wall, which defines the inner diameter, and an outer wall which defines the outer dimensional characteristics, i.e., size, shape, and the like, of the compressed air tank.

The compressed air tank 104 has a top 130, a bottom 132, a front 134, and a back 136. The compressed air tank 104 includes an axis 140, which is the centerline of the compressed air tank 104. In a preferred embodiment, the top 130 is connected with the mounting bracket 106 which connects with the motor 108, and the manifold 112 which through coupling with the motor 108 enables the functionality of the air compressor assembly 100. The manifold 112 may include various gauges and connector assemblies for enabling the use of the compressed air stored within the compressed air tank 104.

In the current embodiment, the compressed air tank 104 is further connected on the bottom 132 proximal to the back 136, with the wheel assembly 120. The wheel assembly 120 provides the air compressor assembly 100 with a transport capability enabling a user to position the air compressor assembly 100 in various locations. It is understood that the current embodiment of the compressed air tank 104 is representative of a horizontal portable tank model for use in a portable air compressor assembly and that vertical portable tank models or other alternative compressed air tank models as contemplated by those of ordinary skill in the art may be employed in operation with the corrosion fuse 200. In further alternative embodiments the corrosion fuse 200 may be employed with stationary compressed air tank assemblies without departing from the scope and spirit of the present invention.

Figure 21:
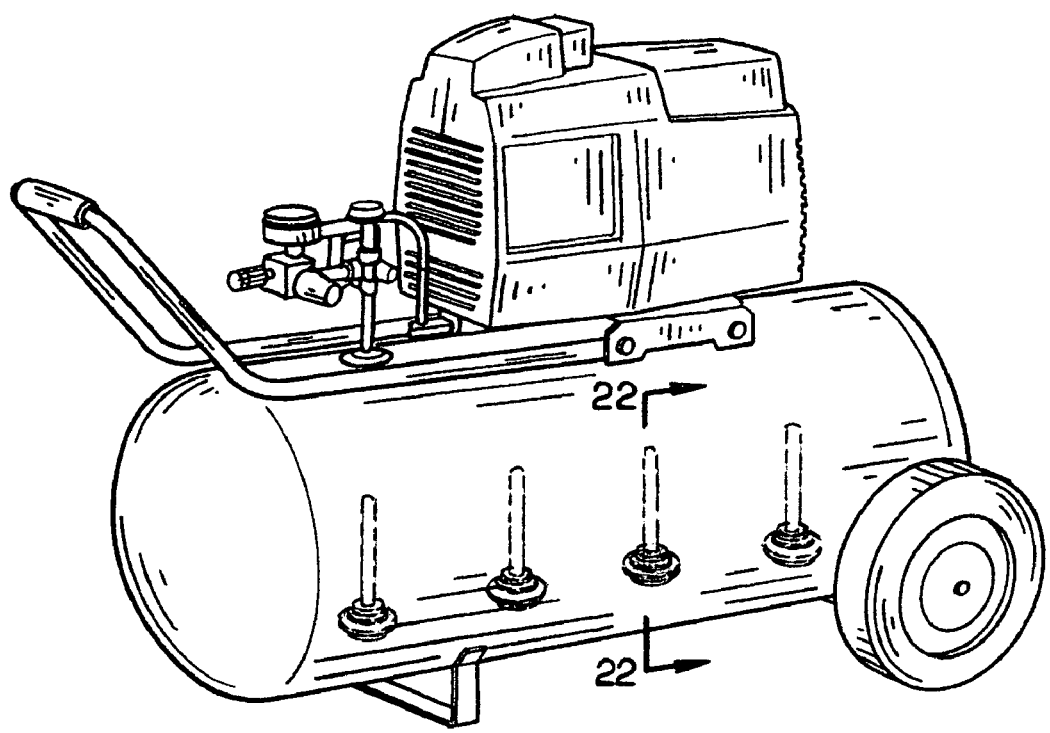
FIG. 21 illustrates an exemplary air compressor assembly employing multiple corrosion fuses for the detection and indication of corrosion occurring within a horizontal compressed air tank in accordance with the present invention.

Disposed along the bottom 132 of the compressed air tank 104 is a tank receiver 150. In a preferred embodiment, the tank receiver 150 is an aperture disposed upon the bottom 132, generally in a position corresponding with a mid-point of the air tank 104, extending from the outer wall through the inner wall of the compressed air tank 104. In the current embodiment, the orientation of the compressed air tank 104 establishes the mid-point as the lowest gravitational point in the air tank 104. The lowest gravitational paint in the air tank 104 being that area within the tank to which gravity will most likely draw moisture (i.e., condensate) and other substances, such as loose media and the like, which may be found within the interior of the compressed air tank 104. Thus, the mid-point is the area within the tank where the accumulation of moisture and media is most likely to occur. It is to be understood that due to the orientation of the compressed air rank 104 the mid-point may not be the lowest gravitational point or may be one of several lowest gravitational points within the air tank and that the accumulation of moisture and/or substances may occur in alternative locations or multiple locations within the air tank. As is shown in FIG. 21 and described below, the corrosion fuse 200 may be established in various locations and/or multiple corrosion fuses may be used to accomplish the indication of corrosive failure.

It is understood that the inner diameter of the tank receiver 150 is constructed to assist in optimizing the connection of a fitting (i.e., flange, weld spud) 204. However, the aperture may be variously configured as contemplated by those of ordinary skill in the art. It is contemplated that the tank receiver 150 may include additional features. For example, the tank receiver 150 may include a cover to assist in avoiding contamination of the interior of the compressed air tank 104 by outside contaminants. The cover may be retractable and/or removed from its connection with the tank receiver 150. The tank receiver 150 may include a connecting mechanism for connecting different mechanical components. For example, the tank receiver 150 may include a quick connect mechanism, a spring loaded lock mechanism, a friction fit mechanism, a snap lock mechanism, a latch mechanism, and the like, which may promote the ease of use of the present invention, for connecting with the cover or various fitting assemblies.

In the current embodiment, the fitting is a flange 204, which provides for the coupling of a plug 208 and corrosion detector 212 of the corrosion fuse 200 with the compressed air tank 104 and at least partially encompasses the tank receiver 150. The flange 204 is welded to the bottom 132 of the compressed air tank 104 and may be commonly referred to as a weld flange. Alternatively, the flange 204 may be coupled with the bottom 132 of the compressed air tank 104 through various coupling techniques and mechanisms as may be contemplated by those of ordinary skill in the art. The flange 204 defines an internally threaded first flange inner diameter 240 and a second flange inner diameter 242. The second flange inner diameter 242 is optimally sized for the operational connection of the flange 204 with the tank receiver 150 and assists in establishing an optimal operational environment for the tank receiver 150 and the corrosion detector 212 of the corrosion fuse 200. It is contemplated that the second flange inner diameter 242 may vary in size to accommodate differently sized tank receivers and corrosion detectors. In a preferred embodiment, the second flange inner diameter 242 may be established in a range of five tenths (0.5") of an inch to fifty five hundredths (0.55") of an inch. Alternatively, the second flange inner diameter 242 may be established in a range of four tenths (0.4") of an inch to one (1.0") inch.

In a preferred embodiment, the flange 204 is welded to the bottom 132, outer wall of the compressed air tank 104 in a location which aligns the flange first and second inner diameters with the tank receiver 150. This positioning allows the flange 204 to sit lower than the outer wall of the air tank 104. Since the flange 204 is welded to the outer wall, the flange 204 avoids exposure to a corrosive environment which may exist within the air tank, and, therefore, the flange 204 and the process and materials used to connect it with the air tank 104 are not required to meet ASME code. Alternatively, the flange 204 may be connected with the outer wall of the air tank 104 through the use of soldering or brazing techniques.

In alternative embodiments, the flange 204 may be variously positioned relative to the compressed air tank 104. For instance, the flange 204 may be connected to both the outer wall and the inner wall of the compressed air tank 104 in the area immediately surrounding the tank receiver 150, forming a portion of the compressed air tank 104 inner and outer walls. In such an embodiment, it is contemplated that the flange 204 and the process and material used to connect the flange 204 to the outer wall of the compressed air tank 104 meet ASME code requirements. Further, the flange 204 may be coupled with the compressed air tank 104 via a secondary mechanical connection mechanisms/systems, such as a mounting bracket connected to the bottom 132 in a position for the proper operational alignment of the flange 204 with the tank receiver 150. The flange 204 may connect with various mechanical connecting mechanisms, such as a quick connect mechanism, a spring loaded lock mechanism, a friction fit mechanism, a snap lock mechanism, a latch mechanism, and the like, which may promote the ease of use of the present invention, connected to or about the tank receiver 150. It if contemplated that various adhesives, such as wicking cement, organic adhesive, and the like, which provide a secure joint and promote the prevention of air and water penetrating the joint may be employed. It is to be understood that the various techniques, such as welding, soldering, brazing, the various mechanical connection mechanisms, such as the mounting bracket and others described above, and the various adhesives, such as the wicking cement, may be used alone or in various combinations with one another in order to meet or exceed ASME code requirements when necessary.

The flange 204 may be composed of various materials with sufficient structural rigidity to enable the functional capabilities of the corrosion fuse 200. In the current embodiment, the flange 204 is composed of similar low carbon steel as that employed for the compressed air tank 104. In alternative embodiments, the flange may be composed of various different steel alloys, metals, and the like. It is further contemplated that alternative materials, such as plastics, composites, and the like, may be employed. These alternative materials may have corrosive compositional characteristics which promote an increased corrosive rate and quicker failure rate of the flange 204 if brought into contact with corrosive media. The quicker corrosion of these alternative materials may assist the user in identifying a corrosive failure occurring within the compressed air tank 104.

In a preferred embodiment, the first flange inner diameter 240 is internally threaded in configuration to connect with the plug 208 of the corrosion fuse 200. It is contemplated that the first flange inner diameter 240 may be variously configured. For example, the first flange inner diameter 240 may enable a snap fit mechanism, whereby the corrosion fuse, once inserted into the first flange inner diameter 240, is affixed by a snap lock assembly. Alternatively, friction fit mechanisms, quick connect mechanisms, spring loaded lock mechanisms, and the like may be employed without departing from the scope and spirit of the present invention. Still further, adhesives such as organic adhesive, wicking cement, and the like, which may promote a secure joint and the prevention of air and moisture from penetrating the joint, may be employed. The various connection mechanisms and adhesives may be used alone or in combination with one another. It is understood that the internally threaded configuration of the current embodiment of the first flange inner diameter 240 may be threaded in a defined section which partially encompasses the area defined by the first flange inner diameter 240.

It is further contemplated that the flange 204 may be integral with the plug 208 and corrosion detector 212 of the corrosion fuse 200. The integral corrosion fuse unit may be connected with the air tank 104 and tank receiver 150 using various techniques, such as welding, soldering, brazing techniques, or any of various connection mechanisms, such as a quick connect mechanism, a spring loaded lock mechanism, a friction fit mechanism, a snap lock mechanism, a latch mechanism, and the like, which may promote the ease of use of the present invention. Still further, adhesives such as organic adhesive, wicking cement, and the like, which may promote a secure joint and the prevention of air and moisture from penetrating the joint, may be employed. The various connection techniques, mechanisms, and adhesives may be used alone or in combination with one another.

In a preferred embodiment, the flange 204 may include a circumferential threading of an outer wall for engaging with the tank receiver 150 which may include an internally threaded inner diameter, as previously described. Other mechanisms for connecting the integral corrosion fuse unit with the tank receiver may be employed, as contemplated by those of ordinary skill in the art.

In a further alternative embodiment, a compressed air tank may include an integral corrosion fuse. For example, during the manufacturing of the compressed air tank an integral corrosion fuse may be formed. The integral corrosion fuse may extend into the interior of the air tank. The integral corrosion fuse may be generally cylindrically configured, such as that for the corrosion detector 212, or may have a variety of different configurations, such as those shown in FIGS. 14-18 and described below. The length of the integral corrosion fuse may be established to extend within the compressed air tank to an expected waterline which may be formed in the compressed air tank. The waterline is formed from condensate accumulation, generally at the lowest point within the compressed air tank. It is understood that the accumulation of condensate typically occurs at the lowest gravitational point due to the force of gravity drawing the condensate or other media to the lowest gravitational point. In the alternative, the length of the integral corrosion detector may extend generally to the centerline of the compressed air tank. It is further contemplated that the length of the integral corrosion detector may extend from the bottom 132 to the top 130 of the compressed air tank.

In alternative embodiments of the present invention, the cap 216 may be variously configured, such as those shown in FIGS. 8 through 12. FIG. 8 illustrates the cap 216 as a plug which is seated and joined against the first end 230 of the corrosion detector 212. The joining may occur using several techniques, preferably an adhesive which expels air and/or moisture and which forms an air tight joint is used, such as wicking cement or organic adhesives. In an alternative example, a cap 216a shown in FIG. 9 is in a configuration where a section of the cap inserts within the inner diameter of the corrosion detector 212. Still further, a cap 216b, shown in FIG. 10, is in a configuration where the cap includes a threaded section which couples with an internally threaded section of the inner diameter of the corrosion detector 212. Additionally, a cap 216c, shown in FIG. 11, is in a configuration where a section of the cap receives at least a section of the corrosion detector 212 within. In this configuration, the cap 216c includes at least a partial sleeve for establishing the connection of the cap 216c with the corrosion detector 212. In a further alternative embodiment, shown in FIG. 12, the sealed or closed first end 230 is formed by crimping the first end 230.

The securing of the cap embodiments shown and described and further alternative which may be contemplated by those of ordinary skill in the art for the closed first end 230 may be assisted by the use of various adhesive materials, such as the wicking cement adhesive previously identified. It is further contemplated that various welding techniques may be employed for sealing the first end 230. For example, the first end of the corrosion detector, shown in FIG. 12, is crimped together and sealed by a welding process. However, a possible drawback of using conventional welding, soldering, or brazing techniques may be the creation of non-uniform corrosion in or near the fusing region. Alternatively, the use either alone or in combination of techniques such as press-fitting, press-fitting plus, organic adhesives, laser welding, or friction welding may be less corrosion prone choices, for providing the sealed first end. It is understood that additional alternative techniques may be employed to seal the corrosion detector 212 as contemplated by those of skill in the art.

The configuration of the corrosion detector 212 may be changed to assist in providing the "leak-before-burst" mechanical advantage of the present invention. For instance, the wall of the corrosion detector 212 may be generally configured in various geometrical shapes, such as those shown in FIGS. 15-18. The different geometric shapes of the corrosion detector 212 may increase the surface area exposed, which may provide an advantage in corrosion detection. In another alternative embodiment, the wall of the corrosion detector 212 may include one or more grooves to assist in promoting increased surface area exposure, as shown in FIG. 14. The one or more grooves may be longitudinal, running the length of the corrosion detector 212 or the grooves may be in a pattern encircling the circumference of the corrosion detector 212. It is further contemplated that various configurations may be employed in combination upon the corrosion detector 212.

In a preferred embodiment, the wall of the corrosion detector 212 is a uniform thickness of thirty-five thousandths (0.035") of an inch. It is understood that the thickness of the wall of the corrosion detector 212 is a predictive indicator of corrosion occurring to the wall of the compressed air tank 104, identified herein as a first corrosion point. Thus, the thickness of the wall of the corrosion detector 212 may be differently configured. For example, the thickness of the wall of the corrosion detector 212 may be a predictive indication that the first corrosion point has been reached, thereby providing a user with an indication that corrosion is occurring in order to assist the user in making a decision about the operation of the compressed air tank 104. The first corrosion point, in the current embodiment, is established in correlation with the thickness of the wall of the corrosion detector 212. At thirty-five thousandths (0.035") of an inch, when the wall of the corrosion detector 212 fails the user is able to predict that at least a portion of the wall of the compressed air tank 104 has corroded by thirty-five thousandths (0.035") of an inch. In an alternative embodiment, the first corrosion point may be determined as a percentage of the thickness of the compressed air tank wall, such that upon failure of the corrosion detector 212 the user is provided an indication of a percentage of corrosive loss which has occurred in at least a portion of the wall of the compressed air tank 104. In an additional embodiment, the first corrosion point may correlate with the thickness of the wall corrosion detector 212 which is determined as a ratio of the thickness of the wall of the compressed air tank 104. For example, the thickness of the wall of the corrosion detector 212 compared to the thickness of the wall of the compressed air tank 104 may be established as a two to one ratio (2:1) where the wall of the corrosion detector is one-half the thickness of the wall of the compressed air tank 104. Alternative relationships, such as a three to one ratio, four to one ratio, and the like may be employed as contemplated by those of skill in the art.

It is contemplated that the thickness of the wall of the corrosion detector 212 may range between twenty thousandths (0.020") of an inch to one tenth (0.1") of an inch. More preferably, the thickness of the wall may range between thirty-five thousandths (0.035") of an inch and fifty-one thousandths (0.051") of an inch. Additionally, the thickness of the wall may be established in accordance with various specification parameters and relationships, such as those identified above, and therefore may have a value below twenty thousandths (0.020") of an inch or above one tenth (0.1") of an inch.

The length of the metal tubing is from the sealed first end 230 to the open second end 232. In a preferred embodiment, the length of the corrosion detector 212 is such that when the corrosion fuse 200 is in operation with the compressed air tank 104 that the first end 230 is generally at a height equal to the centerline 140 of the compressed air tank 104. In an alternative embodiment, the length of the corrosion detector 212 may extend within the compressed air tank 104 to an expected waterline. The waterline being that point along the wall of the compressed air tank 104 which an accumulation of condensate may typically reach. It is understood that gravity will draw condensate to the lowest point within the compressed air tank 104 to accumulate. From this lowest point, the condensate will accumulate and begin to fill or move up the immediately surrounding wall of the compressed air tank 104. It is contemplated that the overall length of the corrosion detector 212 may be between two (2") inches and twelve (12") inches. In the current embodiment, the corrosion detector is five (5") inches in length. It is understood that the length of the corrosion detector 212 may vary and be shorter than two (2") inches and longer than twelve (12") inches in order to assist in promoting the use of the corrosion indicating advantages of the corrosion fuse 200 within variously sized compressed air tanks, without departing from the scope and spirit of the present invention.

The outer diameter of the wall of the corrosion detector 212 may range between two tenths (0.2") of an inch to two (2") inches. In a preferred embodiment, the outer diameter is five tenths (0.5") of an inch. It is understood that in alternative embodiments the outer diameter may be less than two tenths (0.2") of an inch or greater than two (2") inches. The inner diameter of the wall of the corrosion detector 212 may range between one tenth (0.1") of an inch to one and a half (1.5") inches. In a preferred embodiment, the inner diameter is four hundred sixty-three thousandths (0.463") of an inch. It is understood that in alternative embodiments the inner diameter may be less than one tenth (0.1") of an inch or greater than one and a half (1.5") inches.

In an alternative embodiment, the inner diameter of the wall of the corrosion detector 212 may be in a non-uniform configuration. For instance, the inner diameter of the wall may include areas of increased and/or decreased thickness of material. These different configurations may be based upon desired characteristics to be achieved by the inner diameter. For instance, a narrower inner diameter provided in various locations may assist in promoting the flow of compressed air and water through the inner diameter. This may promote a quicker recognition of corrosive failure within the compressed air tank 104. It is also contemplated that the outer surface of the corrosion detector wall may have different structural properties than the inner surface of the wall. For instance, the outer surface may include various coatings, treatments, and the like, to provide different corrosive failure rates, while the inner surface may include coatings which promote a decrease in the frictional co-efficient experienced by escaping air, water, and/or other media upon the occurrence of a corrosive failure of the corrosion detector wall. For example, the inner wall may be Teflon coated to reduce frictional forces experienced by the escaping air, water, and/or media, via the inner chamber of the corrosion detector 212.

Various coatings, applications, treatments, and the like, having a variety of chemical properties, may be disposed upon the inner and outer walls of the corrosion detector 212 to assist in promoting the proper functioning of the corrosion fuse 200.

Further, it is contemplated that the configuration given to the corrosion detector 212 may be, at least partially, determined by characteristics of the compressed air tank in which it is to be employed. For instance, the compressed air tank may be of such a size that the volume of stored compressed air typically equals more than is used for a particular application. It may be that the compressed air tank stores, possibly for extended periods of time, an amount of compressed air which over time condenses, causing moisture to accumulate and establishing a "waterline attack" in a generally similar area within the compressed air tank. Thus, for example, the corrosion detector 212 may be configured to include a bulbous region generally established at an expected "waterline attack" level, which may advantageously expose a greater surface area to corrosive attack. In alternative embodiments, changes to the configuration as described above may be in various locations along the corrosion detector 212 in order to assist in providing optimal corrosive failure rate determination. For example, the corrosion detector 212 may include multiple bulbous regions disposed in various locations along its length between the first and second ends.

The second end (i.e., "open" end) 232 of the corrosion detector 212 provides for the flow of substance from the interior of the compressed air tank, through the inner chamber of the corrosion detector 212, and finally out into the environment, once corrosion has caused the wall of the corrosion detector 212 to fail and air/media to leak through. The air/media simply leaks out the second end 212 providing an indication to a user of the present invention, as shown in FIG. 19. It is contemplated that various indication systems, i.e., visual and audible, may be included with the corrosion detector 212 to assist a user in identifying corrosive failure without departing from the scope and spirit of the present invention. For example, a rubber diaphragm (i.e., balloon) may be included within the interior of the corrosion detector 212 and upon corrosive failure the rubber diaphragm is forced to extend out the second end 232 providing a visual indication of failure. Alternatively, the interior of the corrosion detector 212 may be coated with a water activated dye. When corrosive failure occurs and water begins to leak through the corrosion detector 212 to the outside environment the water will appear colored to assist in the visual identification of the corrosive failure. In another example, a visual sensor assembly may be employed as a visual indication system, the visual sensor assembly providing a visual indication when it is contacted by leaking fluid or escaping air from the corrosion detector 212. The visual sensor assembly includes a plate proximately positioned below the open second end 232 and plug 208. The plate is designed to be contacted by escaping air, water, and/or other media. The plate is electronically linked with a display device so that when the plate is contacted by escaping substances it triggers the display device to provide a visual indicator which is visually ascertainable by the user. The display device may be a set of light emitting diodes (LED) connected with the handle 116 of the air compressor assembly 100. Alternative design configurations for the plate and display device as contemplated by those of ordinary skill in the art may be employed. The corrosion detector 212 may be constructed such that upon the occurrence of a leaking of air an audible noise, such as a whistling noise, is generated. Thus, the user may hear a whistling indicator of corrosive failure.

The second end 232 includes an outer surface which connects with the plug 208. In a preferred embodiment, the outer surface of the second end 232 of the corrosion detector 212 may connect with the plug 208 via a welding process. However, due to drawbacks previously identified of using conventional welding, soldering, and brazing techniques, alternative techniques, such as the use of an organic adhesive, laser welding, and the like, described previously, may be employed. For instance, the second end 232 may be connected with the plug 208 including the use of adhesives, such as wicking cement adhesive, which may provide advantageous characteristics such as the prevention of unwanted materials, like air or moisture, from getting into the joint. In the alternative, the second end 232 may be threaded in configuration for connecting with a threaded plug. Such a threaded connection may employ right handed or left handed threading and may be used in conjunction with any of the above mentioned processes, adhesives, and/or techniques. Further, other connecting mechanisms, such as a quick connect mechanism, a spring loaded lock mechanism, a friction fit mechanism, a snap lock mechanism, a latch mechanism, and the like, which may promote the ease of use of the present invention, may be employed without departing from the scope and spirit of the present invention.

The configuration of the outer surface, and thusly the outer diameter, may be altered. For instance, a flange which may provide an optimal fit with a particular compressed air tank may require a differently sized plug than the exemplary plug 208 shown throughout FIGS. 1 through 10. Thus, the second end 232 may have to be re-configured, relative to the rest of the corrosion detector 212 in order to accommodate a connection with a differently configured plug.

In the current embodiment, the inner diameter established by the second end 232 is uniform to the inner diameter established throughout the corrosion detector 212. In the alternative, the inner diameter established by the second end 232 may be variously configured to accommodate a wide range of needs. For instance, the inner diameter may include a funnel or ramp resulting in a narrowing of the inner diameter as the corrosion detector 212 proceeds from the first end 230 towards the second 232. The funnel/ramp may promote the flow of substance out into the environment from within the inner diameter of the corrosion detector 212.

The plug 208, via a mechanical connection with the flange 204, provides the mechanical coupling of the corrosion detector 212 with the flange 204 and seals the first flange inner diameter 240. In the current embodiment, the plug 208 is a partially threaded connector having an overall length of five hundred thirty three thousandths (0.533") of an inch and a plug axis 260, which is a centerline of the plug 208. The width of the plug 208 being six hundred seventy five thousandths (0.675") of an inch. It is understood that the length and width of the plug 208 may be varied to accommodate connection with the corrosion detector 212 and the flange 204. Thus, the length of the plug 208 may range between two tenths (0.2") of an inch to two (2") inches. The width of the plug 208 may be established from two tenths (0.2") of an inch to two (2") inches. It is contemplated that the length and width of the plug 208 may vary, for instance at less than two tenths (0.2") of inch or greater than two (2") inches.

In a preferred embodiment, the plug 208 assists in promoting the second end 232 of the corrosion detector 212 being open to the outside environment by a plug first inner diameter 224 and a plug second inner diameter 226 in operational concert with the second end 232 of the corrosion detector 212. In a preferred embodiment, the plug first inner diameter 224 and second inner diameter 226 are aligned along the centerline 260 of the plug 208 and the corrosion detector centerline 270 is aligned with the plug centerline 260, as shown in FIG. 5. A bottom section of the plug includes the plug first inner diameter 224. In a preferred embodiment, the plug first inner diameter 224 is two hundred seventy five thousandths (0.275") of an inch. It is understood that the plug first inner diameter 224 of the bottom section may be variously sized, such as between one tenth (0.1") of an inch and one (1") inch. Alternatively, the size of the plug first inner diameter 224 may vary to accommodate the needs of a user or manufacturer, thus the plug first inner diameter 224 may be less than one tenth (0.1") of an inch or more than one (1") inch.

In the current embodiment, a top section of the plug 208 extends to a depth of one hundred twenty five thousandths (0.125") of an inch within the plug 208. The top section includes a wall thickness of forty-five hundredths (0.45") of an inch. A top surface of the top section includes a mechanical connection. In the current embodiment, the mechanical connection is a first receiver 220 and a second receiver 222. The first and second receivers are slots within the top surface of the bottom section, having a width of fifteen hundredths of an inch and a depth of one tenth of an inch. It is understood that the width and depth of the first and second receivers may vary as contemplated by one of ordinary skill in the art. The first and second receivers allow the user to engage a mechanical device within the receivers. In a preferred embodiment, the first and second receivers are capable of being engaged by a key or a spanner wrench to secure the plug 208 within the flange 204. It is understood that the first and second receivers may be configured to be engaged by a non-standard mechanical device. Other alternative configurations, such as enabling the receivers as tabs extending from the top surface for engagement by a mechanical device or as multiple apertures for engagement by a mechanical device are contemplated by the present invention.

It is contemplated that the corrosion fuse 200 provides tamper resistant features. For instance, the first and second receivers may be variously configured to accommodate the securing of the plug 208 within the flange 204 and avoiding unwanted tampering. For example, the receivers may be configured in a manner which may assist in avoiding the removal of the plug 208 from the flange 204 by a user of the present invention. The receivers may be configured as a slot with a slanted ramp terminating at a particular depth on a clockwise end of the slot. This may enable the securing of the plug 208 within the flange 204 and prevent the plug 208 from being removed.

The bottom section is integrally connected with the top section in the current embodiment. Alternatively, the plug 208 may include separate, connectable sections. The number and size of the sections of the plug 208 may be varied as contemplated by those of skill in the art to accommodate operational connections with variously sized flanges and corrosion detectors. The bottom section includes a wall thickness of one hundred twenty five thousandths (0.125") of an inch. Further, the current embodiment of the bottom section, has a length which may range between two tenths (0.2") of an inch to five tenths (0.5") of an inch. A more preferred range for the length of the bottom section is between four hundred ten thousandths (0.410") of an inch and three hundred seventy thousandths (0.375") of an inch. More particularly, a first preferred embodiment, the length of the bottom section is three hundred seventy five thousandths (0.375") of an inch. The bottom section has an outer surface which is that section of the plug 208 threaded for engagement with the flange 204.

As previously described, the plug 208 establishes a threaded connection with the flange 204. It is to be understood that the number of threads, depth of threads, and the orientation of the threads (i.e., right or left handed threads) on the plug second wall corresponds with the number, depth, and orientation of threads/grooves established on the fitting. The alternative threading patterns with which the plug 208 and flange 204 are allowed to be constructed with may provide a further tamper resistant feature to the present invention. Further, it is contemplated that various mechanical coupling assemblies may be employed in order to couple the plug 208 and flange 204. These mechanical connection assemblies may include a quick connect mechanism, a spring loaded lock mechanism, a friction fit mechanism, a snap lock mechanism, a latch mechanism, and the like, which may promote the ease of use of the present invention.

The bottom section of the plug further includes an inner surface which defines the plug second inner diameter 226. The plug second inner diameter 226 allows the plug 208 to connect with the second end 230 of the corrosion detector 212. In a preferred embodiment, the plug second inner diameter 226 is five tenths (0.5") of an inch. It is contemplated that the plug second inner diameter 226 may be between one and a half (1.5") inches and one tenth (0.1") of an inch. It is understood that the plug second inner diameter 226 may be variously determined by user and/or manufacturers, thus, the plug second inner diameter 226 may be less than one tenth (0.1") of an inch or greater than one and half (1.5") inches without departing from the scope and spirit of the present invention.

In operation, the plug second inner diameter 226 engages and connects around the outer surface of the second end 232 of the corrosion detector 212 while the plug first inner diameter 224 provides the passage through which the second end 232 of the corrosion detector 212 is exposed to the outside environment. It is understood that the configuration of the plug 208, including the first and second inner diameters, may be varied to accommodate alternative connection configurations with the corrosion detector 212.

Figure 20:
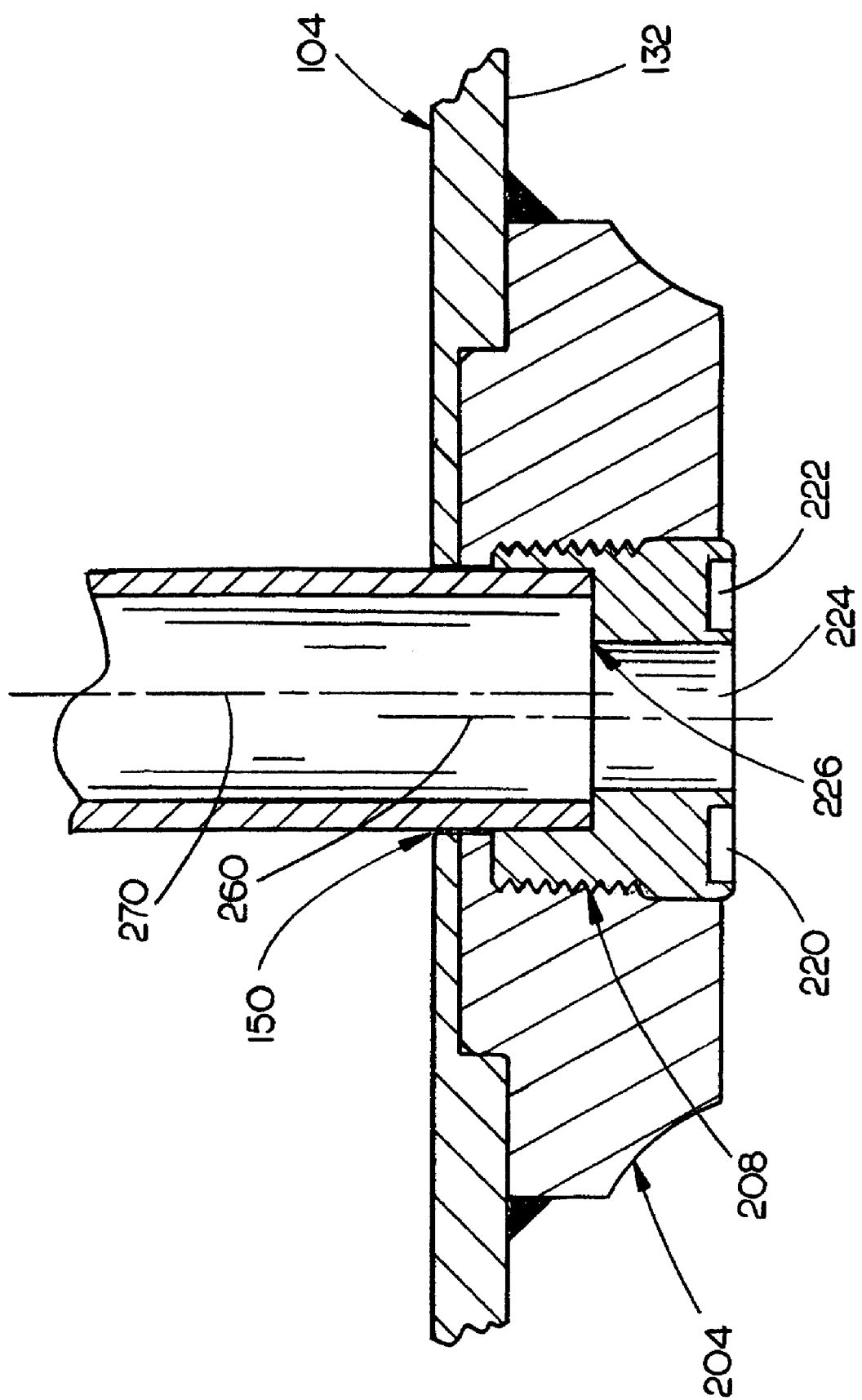
FIG. 20 is an expanded cross-sectional view illustrating the joining of the corrosion fuse with a compressed air tank.

An additional tamper resistant feature of the corrosion fuse 200 is providing the plug second inner diameter 226 in an offset position relative to the centerline 260 of the plug 208, as shown in FIG. 20. The offset second inner diameter 260 connects the corrosion detector 212 in a manner whereby the corrosion detector centerline 270 is offset from the plug centerline 260. This offsetting of the plug second inner diameter 226 may promote decreased tampering, such as the drilling of the plug 208, by users. With an offset plug second inner diameter 226 if drilling of the plug 208 were to occur it may result in a drilling of the threads which connect the plug 208 with the flange 204, possibly rendering the plug 208 inoperable for its intended purpose. Having such a tamper resistant feature may assist in promoting the proper use of the corrosion fuse 200. The configuration of the plug first inner diameter 224 and the second end 230 of the corrosion detector 212 may not be required to be altered and may connect with an offset plug second inner diameter 226. It is contemplated that an offset configuration for the plug second inner diameter 226 may include changes in the configuration of the plug first inner diameter 224 and the second end 230 of the corrosion detector 212.

It is further contemplated that the flange 204, plug 208 and/or corrosion detector 212 may include a sensor assembly as an alternative tamper resistance feature. The sensor assembly may be communicatively linked with an information handling system, such as a computing device (i.e., PC, lap-top computer, handheld computer, PDAs, etc . . . ) which may display to the user of the corrosion fuse 200 a tampering warning when tampering is detected by the sensor assembly.

The sensor assembly may be linked with a mechanism disposed within the corrosion fuse 200 (including the flange 204) which may activate upon the detection of tampering by the sensor assembly. For instance, a mechanism for releasing a sealant may be linked with the sensor assembly and when tampering is detected the sealant is released, effectively closing/sealing the inner chamber of the corrosion detector 212 from the outside environment. This may be of benefit to users who unknowing tamper with and damage the corrosion fuse 200 as it may provide a mechanism through which the integrity of the compressed air tank may be maintained, at least temporarily, to possibly decrease the risk of a catastrophic failure. A mechanism linked with the sensor assembly may alternatively cause the rupturing of the wall of the corrosion detector 212 or a rupturing of the sealed joint between the corrosion detector 212 and the plug 208. Thus, when tampering is detected by the sensor assembly, the corrosion fuse 200 is caused to fail, rendering the compressed air tank within which it is employed in operable.

Further, the configuration of the plug 208 may be varied to assist in providing an increased effectiveness in the identification of corrosive failure occurring within the compressed air tank. For instance, a narrower plug first inner diameter may provide for a more effective flow of substances from within the compressed air tank, which have corroded through the wall of the corrosion detector 212, to the outside where the presence of the substance may be observed. Alternatively, the plug 208 may be constructed to provide an audible noise, such as a whistling, so that the escape of air causes an audible indication of corrosive failure to a user.

Material selection for the corrosion fuse 200, in particular the corrosion detector 212 and the plug 208, may vary according to the needs of the user, manufacturer, and/or the compressed air tank, such as the compressed air tank 104, within which the corrosion fuse is to be employed. Generally, similar materials may be used to manufacture the compressed air tank and corrosion fuse 200. This may promote a similar corrosive failure rate between the compressed air tank and corrosion detector 212 of the corrosion fuse 200. This may further promote predictability of corrosive failure between the corrosion fuse 200 and the compressed air tank. As previously described, the corrosion fuse 200, upon corrosive failure, may indicate a predicted level of corrosion which has occurred within the compressed air tank 104. In the current embodiment, with the wall thickness of the corrosion detector 212 established at thirty-five thousandths (0.035") of an inch, when the corrosion detector 212 fails due to corrosion the user may be able to predict that thirty-five thousandths of an inch of corrosion has occurred within the compressed air tank 104 as well, as stated previously.

In alternative embodiments, the material selected for the corrosion detector 212 may be different from the material selected for the compressed air tank. This may provide advantageous characteristics for the corrosion detector 212 relative to the compressed air tank with which it is employed. For instance, the material of the corrosion detector 212 may have a higher corrosive rate, which may be desired in order to provide an earlier indication of corrosion occurring within the compressed air tank. It is further contemplated that the corrosion detector 212 may be coated with various substances in order to affect the corrosive rate of the corrosion detector 212. For instance, the corrosion detector 212 may be coated with a zinc compound which may affect the corrosive failure rate of the corrosion detector 212. This coating may enable the corrosion detector 212 to be manufactured using alternative materials than those previously identified.

In a preferred embodiment, the compressed air tank 104 is composed of SA-414 Grade G steel. Thus, the corrosion fuse 200 may be composed of the same SA-414 Grade G steel. Different alloys of this general class of steel may corrode similarly in a specific corroding medium, such as water. The corrosion fuse 200 may, therefore, be made from an alloy in this general classification of steel with the possible exception of some alloys which are altered slightly to improve corrosion resistance. It is understood that these alloys may contain small amounts of copper, typically less than 0.02%, and are covered by SA-414 Grade G. When employing alloys containing small amounts of copper it may be beneficial to ensure that the corrosion fuse 200 and the compressed air tank, such as the compressed air tank 104, contain similar amounts of copper. This may promote a similar corrosion rate between the corrosion fuse 200 and the compressed air tank within which it is employed.

In FIG. 21, an air compressor assembly 2100, similar in all respects to the air compressor assembly 100, is shown. Air compressor assembly 2100 differs from air compressor assembly 100 in that the compressed air tank 2104 is connected with a corrosion detection system 2200 comprising a plurality of corrosion fuses 2202, 2204, 2206, and 2208. The plurality of corrosion fuses 2202 through 2208 is similar in every respect to the corrosion fuse 200 of the air compressor assembly 100.

An advantage of the corrosion detection system 2200 is that it provides a mechanism for corrosion detection and indication where the accumulation of moisture and/or other media may be in one or more locations within the compressed air tank 2104. The accumulation of moisture and/or media in multiple locations or in a location not generally corresponding with the mid-point, described previously in reference to the compressed air tank 104, of the compressed air tank 2104 may be the result of several factors. For example, the interior of the compressed air tank 2104 may be uneven due to the manufacturing process, wear through use, physical damage, and the like which cause the interior to have an uneven pattern. In addition, the air compressor assembly 2100 may be engaged upon an uneven surface causing the compressed air tank 2104 to be angularly displaced from a horizontal position. Any of the above factors and others which may be contemplated by those of ordinary skill in the art may cause the accumulation of moisture and/or media in various locations throughout the interior of the compressed air tank 2104.

With the addition of multiple corrosion fuses to the compressed air tank 2104, the detection and indication of corrosive activity within the air tank 2104 may be increased. This may result in notification to a user of the air compressor assembly 2100 of a failed compressed air tank 2104 due to corrosion, where alternative systems, such as the "tell-tale hole" system, may fail to give a user any notification that corrosive activity is occurring. The corrosion detection system 2200 may also promote the use of air compressor assembly 2100 in environments where its use may not typically occur due to such issues as angular displacement of the compressed air tank 2104 and the inability of alternative corrosion detection systems to function.

The positioning of the plurality of corrosion fuses 2202 through 2208 may be varied to accommodate the needs of the manufacture and the end user. The number and dimensional characteristics of the plurality of corrosion fuses employed may also be varied, similar to the variable capabilities described previously in reference to corrosion fuse 200.

It is contemplated that the corrosion detection system 2200 may be employed on various other air compressor assemblies, such as a vertical tank air compressor assembly. In such an embodiment, the plurality of corrosion fuses may be positioned not only along the horizontal axis established by the end cap of the compressed air tank but also along the vertical axis established by the side walls of the vertical compressed air tank.

The plurality of corrosion fuses employed in the corrosion detection system 2200 may include similar tamper resistant features as those described for corrosion fuse 200. In addition, the corrosion detection system 2200 may include a tamper resistant feature, whereby if one of the pluralities of corrosion fuses is tampered with all of the corrosion fuses are hindered in their proper functioning or rendered incapable of proper functioning. For example, the plurality of corrosion fuses may include sensor assemblies which are linked to one another. Thus, the sensor assembly of one corrosion fuse which is being tampered with may send a signal to all corrosion fuses. The signal may activate a mechanism disposed within each of the corrosion fuses which hinders their proper functioning or renders them incapable of proper functioning. The mechanism may activate the release of a sealant which fills the inner chamber of the corrosion fuses, effectively sealing/closing the second end of the corrosion fuses. Alternatively, the mechanism may cause a rupture of the wall of the corrosion fuse or a rupture in the sealed joint between a corrosion detector and plug of the corrosion fuse. This rupturing may lead to leaking by one or more of the corrosion fuses, thereby increasing the difficulty of a user being able to maintain the storage capabilities of the compressed air tank.

It is further contemplated that the sensor assembly, of an individual corrosion fuse, may be communicatively linked with an information handling system, such as a computer, handheld PDA (Personal Digital Assistant), and the like for remote monitoring of the corrosion fuse. Thus, any tampering or failures experienced by the corrosion fuse, which is detected by the sensor assembly, may be transmitted to a user of the air compressor assembly even if the user is geographically separated from the air compressor assembly.

Referring now to FIG. 23, a vertical portable air compressor assembly 400 is shown. The air compressor assembly 400 includes an air tank 404 connected with a motor 408 and a manifold 412. The air tank 404 is further connected with a wheel assembly 420 and a handle 416 in order to promote the portability of the air compressor 400. A corrosion fuse 450 is coupled with the air tank 404 to provide for the detection of corrosion occurring within the air tank 404. It is understood that the corrosion fuse 450 is similar in every respect to the corrosion fuse 200. With the air tank 404 established in a vertical orientation for operation, the corrosion fuse 450 is inserted into the air tank 404 through the end cap which forms the bottom of air tank 404. The end cap of air tank 404 may include a tank receiver similar in every respect to tank receiver 150 previously described.

It is contemplated that the corrosion fuse 450 may provide a corrosion detector of varying length/height to accommodate its use in a vertical air tank 404 by generally extending to the center line of the air tank 404. For instance, the corrosion fuse 450 may establish the corrosion detector with a length/height between five (5") inches and thirty-six (36") inches. In a preferred embodiment, the length/height of the corrosion detector of the corrosion fuse 450 is established between twelve (12") inches and twenty-four (24") inches. It is further contemplated that the corrosion fuse 450 may be inserted into various locations about the air tank 404 or that multiple corrosion fuses, such as that shown and described in FIG. 21, may be connected to the air tank 404.

The corrosion fuse 200 and 450 may be utilized as sacrificial devices, intended for use with a single compressed air tank and upon corrosive failure to be disposed of along with the air tank. This may promote increased safety in the use of these types of compressed air tanks in the various assemblies for which they are employed, such as air compressor assemblies. By using the same material for the corrosion fuse as that used for the compressed air tank the corrosive failure rate for the compressed air tank, in which the corrosion fuse is employed, may be established. The following provides examples of the use of corrosion fuses of the present invention within numerous compressed air tanks, identifying corrosive failure rates for the corrosion fuses and the compressed air tanks. Further, the description provided below identifies some of the hazards associated with the use of compressed air tanks and how the corrosion fuse of the present invention may assist in avoiding catastrophic failure due to neglect of these hazards.

Testing Procedures

The approach used to evaluate the effectiveness of the corrosion fuse 200 of the present invention, was to corrode tanks (i.e., compressed air tanks) containing corrosion fuses in an accelerated test. After the corrosion fuses leaked, the corrosion damage to the tank was evaluated by a hydrostatic burst test and wall thickness measurements of the tank. A total of twelve tanks were tested.

Figure 22:
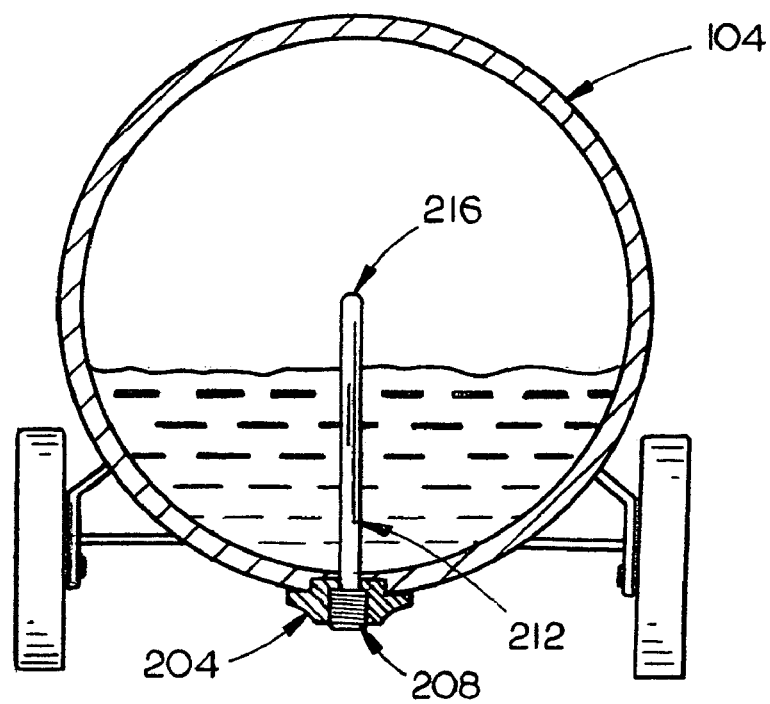
FIG. 22 is a cross-sectional view of the air compressor assembly of FIG. 21 indicating one of the corrosion fuses extending within the air tank and showing that the corrosion fuse generally extends to the centerline of the air tank.

Each tank contained four corrosion fuses, as shown in FIG. 21. Inclusion of multiple corrosion fuses within a single pressure vessel may be preferable in situations where the pressure vessel is being established in a position which is not level. For instance, the pressure vessel may be established on a slanting surface which may cause condensate to accumulate in a particular location, i.e., lowest point, of the pressure vessel. Having the multiple corrosion fuses may accommodate the natural tendencies of condensate to accumulate at the lowest point within the compressed air tank and provide a predictive indicator of corrosion occurring within the compressed air tank. The corrosion fuse including a length of metal tubing (corrosion detector) may be of the same basic composition as the compressed air tank of the air compressor itself. The tube being of much thinner material than the air tank but more robust due to its smaller diameter and shorter length. The tube is connected to a plug and, via the plug connecting with the flange, threaded through the bottom of the air tank with the tube protruding upward inside the air tank. The goal was to select corrosive media that caused a thirty-five thousandth of an inch (0.035") wall tube to corrode through in two, four, and eight weeks. As shown in FIGS. 19 and 22, the corrosion fuses 200 may be subjected to varying levels of corrosive media. The different levels of the media within the air tank establish varying "waterline attack" regions with respect to the air tanks and the corrosion fuses. The present invention may provide the significant advantage of indicating corrosive failure rates at varying levels within the air tank due to its configuration. This may assist in avoiding problems such as catastrophic failure of the air tank. Due to some premature failures, six additional air tanks were tested, but they were corroded at the fastest corrosion rate, attempting to corrode through the fuse in two weeks or less. This provided more data but did not allow for corrosion result data to be gathered for approximately eight weeks.

The corrosion fuses of the present invention were used to conduct this testing. The corrosion fuses were manufactured from a five inch long, three-eighths inch outside diameter metal tubing which was joined to a threaded plug with a hole drilled through it. The other end of the tube was sealed. Four fittings (flanges) were welded to the bottom of the test air tanks and the plug portion of the corrosion fuses was threaded into the fittings.

Potentio-dynamic polarization tests in different strength of sulfuric acid were used to screen candidate corrosive solutions. After eight polarization tests, a corrosion rate of 900 millimeters per year or thirty-five thousandths (0.035") of an inch in two weeks was measured using a one molar solution of sulfuric acid in water. Corrosion rates of one-half and one-fourth these values were estimated for 0.5 and 0.25 molar solutions of sulfuric acid. A constant corrosion rate could not be maintained for the duration of the test because of depletion of the acid. Thus, the solution was replenished every three to four days.

When a corrosion fuse failed, all fuses were removed and their diameters measured using a dial caliper. The air tank was then burst in a hydrostatic test. The burst air tank was then cut into several pieces and the wall thickness was measured using a pointed micrometer. The pointed micrometer could be used to accurately measure the depth of pits and areas of localized corrosion. The corrosion rates of the air tank and all four corrosion fuses were compared.

Some small section of the metal was cut from some air tanks. These sections were mounted, polished, and etched for examination using a metallograph. In addition, samples of the air tank sheet metal were analyzed for chemical composition along with the corrosion fuse material.

Localized corrosion in the air tank that produces long, thinned areas makes these areas weaker than the rest of the air tank. Because the hoop stress is twice the longitudinal stress, It has been postulated that the actual failure pressure at a thinned area will be higher than predicted using the minimum thickness as above due to notch strengthening. The amount of notch strengthening may be difficult to predict and may depend on the details of "notch" geometry. The testing outlined below may provide a more accurate assessment of possible notch strengthening and may enable a determination of the level of notch strengthening.

Enhanced corrosion at welds, a problem identified throughout this specification, may have different effects depending on the direction of the weld. First, the pressure in an air tank causes a hoop stress twice as large as the longitudinal stress. Any corrosion groove along longitudinal welds below the water level may be clearly more susceptible to rupture than girth welds below the water level at the end caps (or heads) of the air tank. Second, water levels tend to be low so the length of girth weld exposed to water is small compared to the length of a longitudinal weld. This may be important in terms of the fracture mechanics of a rupture process. Assuming a condition where the air tank wall almost corrodes through, the corroded groove simulates a crack. For a girth weld corrosion groove (crack), the length is shorter and the stress is lower than the stress level and groove (crack) length of a longitudinal weld corrosion groove. Thus, longitudinal welds may be more prone to corrosive failure than girth welds.

Results

1. Repeatability of Corrosion Fuse Corrosion: The diameter variation of all corrosion fuses measured after the end of each test is listed in Table 1, as follows:

| DIAMETER VARIATION OF CORROSION FUSES | | | | | |
|---|---|---|---|---|---|
| 1-1* | 2-1 | 1-2 | 2-2 | 1-3 | 2-3 |
| .339-.327 | .330-.317 | .335-.326 leak | .343-.341 | .332-.325 leak | .355-.353 |
| .338-.326 | .325-.319 | .336-.328 | .350-.349 | .336-.330 | .350-.345 |
| .339-.326 | .332-.317 | .333-.324 | .342-.339 | .333-.323 | .353-.349 |
| .340-.327 leak | corroded thru, broke off | .336-.327 | .355-.357 | .337-.331 | hole @ weld .357-.354 hole @ weld |
| 1-4 bottom seam | 2-4 | 1-5 | 2-5 | 1-6 | 2-6 |
| .375-.374 | .372-.370 | .351-.346 | .345-.340 | .351-.347 | .342-.334 leak |
| .375-.374 | .372-.371 | .336-.328 leak | .345-.341 | .337-.332 leak | .340-330 leak |
| .375-.374 | .371-.370 | .337-.325 leak | .346-.341 | .336-.333 | .338-.332 leak |
| .375-.374 | .371-.371 | .336-.332 leak | .346-.339 leak | .338-.333 | .338-.331 |
| 1-4 upside down | 2-4 upside down | | 2-5 2nd fuse | 1-6 2nd fuse | |
| .335-.321 | .335-.318 | | .349-.348 | .367-.366 | |
| .358-.327 | .320-.314 | | .348-.346 | .368-.367 | |
| | | | .348-.345 | .367-.367 | |
| | | | .348-.346 | .368-.366 stopped before leak | |

*designates the tank and test conditions.

new air tanks typically burst by a crack forming in the length of longitudinal direction. Thus, thinned areas aligned in the longitudinal direction are more likely to fail due to internal pressure than those aligned in the hoop direction. The simplest method to predict the remaining strength of an air tank with a longitudinal groove in the sidewall is to ratio the remaining thickness to the original wall thickness. This ratio is equated to the ratio of the expected burst strength to the burst strength of new air tanks.

Figure 24:
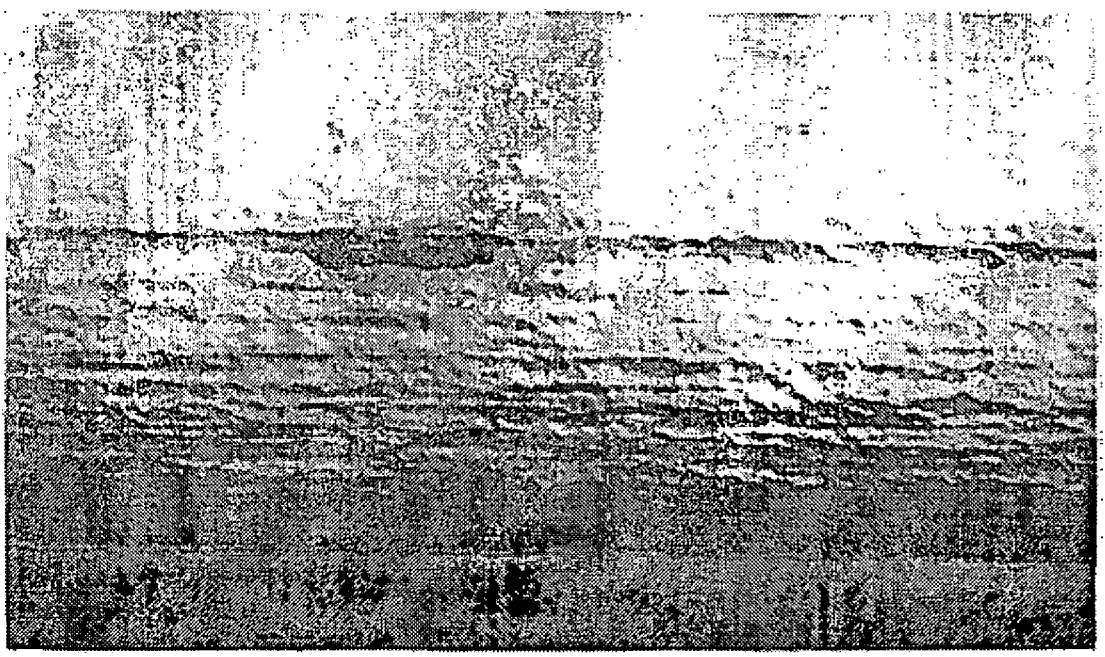
FIG. 24 is an expanded view of a corrosion detector of a corrosion fuse illustrating the non-uniform corrosion that typically occurs.

The range recorded for each corrosion fuse is for the areas that seemed to have uniform corrosion. Corrosion was typically non-uniform as may be seen in FIG. 24. Many of the corrosion fuses that leaked had some structural integrity and typically had diameters, as measured by a caliper, indicating twenty millimeters of metal loss in a corrosion fuse with a thirty-five millimeter wall thickness. This indicates that the corrosion fuses typically had localized pits or grooves about ten millimeters deep when they leaked.

The condition of the corrosion fuses appears to influence the corrosion rate near the threaded end. Diameter measurements in these obviously influenced regions were not recorded. All three joining techniques used to connect the corrosion fuse with the threaded fitting resulted in localized corrosion. There was no attempt to characterize this localized corrosion. Applying a lacquer coating to prevent "early" leaks was used to circumvent localized corrosion at the joint.

Figure 25:
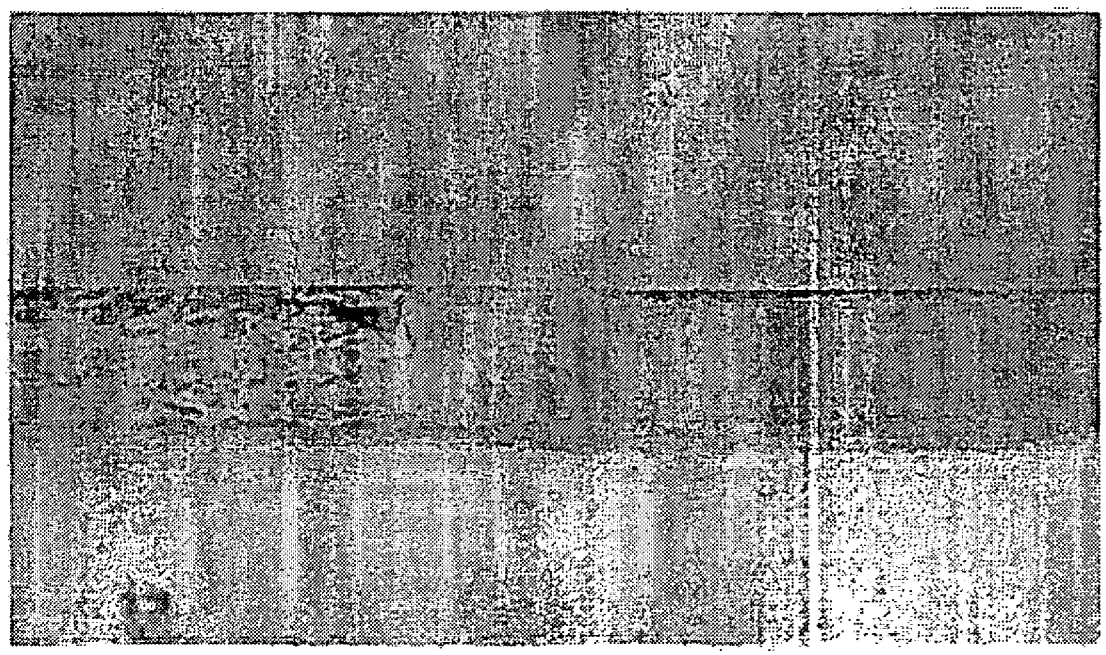
FIG. 25 is a view of a corrosion detector illustrating a change in the wall thickness (diameter) of the corrosion detector.
Figure 26:
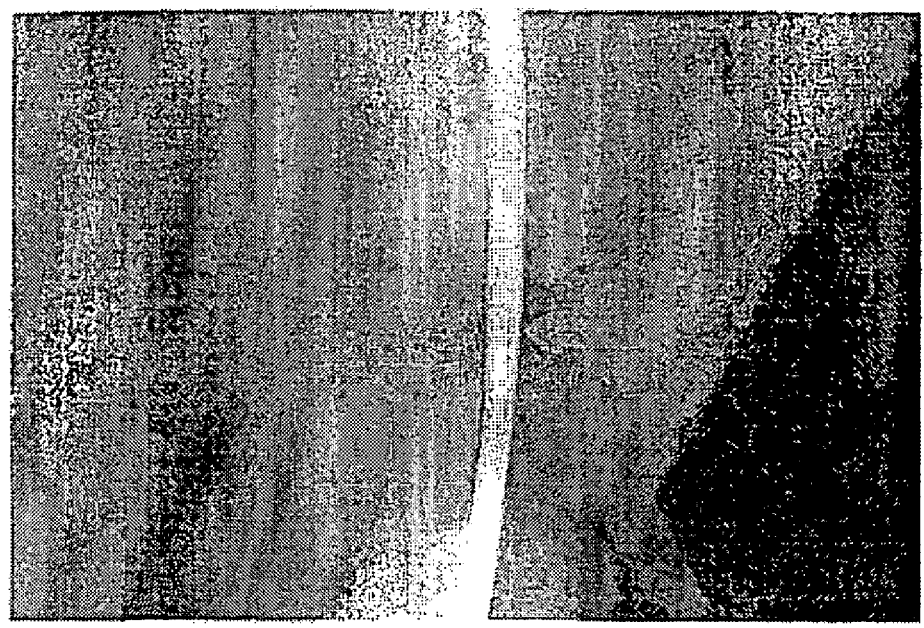
FIG. 26 is a view of a compressed air tank illustrating a change in the wall thickness of the compressed air tank at the corrosion fluid "waterline"
Figure 27:
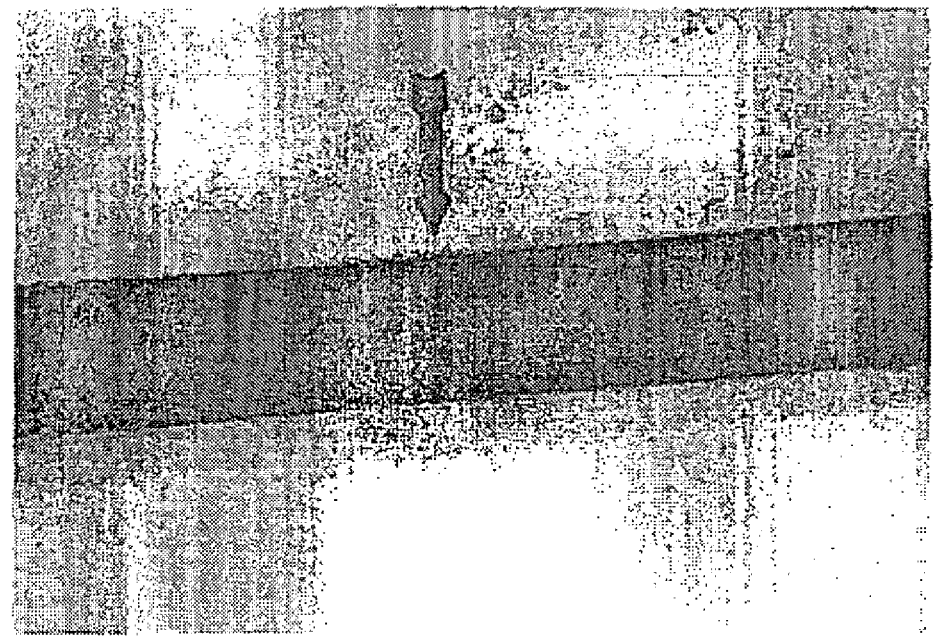
FIG. 27 is a view of a corrosion detector illustrating a change in the wall thickness (diameter) of the corrosion detector at the corrosion fluid "waterline"

2. Fuse and Tank Corrosion Comparison: The well-defined change in fuse diameter after testing is illustrated in FIG. 25. Similar diameter changes in wall thickness of the air tank at the corrosion fluid "waterline" are shown in FIG. 26. The slight groove or localized higher corrosion at the waterline may be seen in this view of the corrosion at the waterline. This level of localized corrosion at the waterline is only slightly greater than the general corrosion. It was common to see localized corrosion at the waterline for the air tanks, but was rare to see localized corrosion of the corrosion fuses. FIG. 27 shows one of these rare cases.

For the corrosion data reported in Table 1, the repeatability (variation of fuse-to-fuse corrosion in a single air tank) of corrosion fuses appears to provide positive results and may provide a more effective corrosive failure rate determining system than those provided previously. Comparing the smallest diameters of corrosion fuses in a single air tank, the largest standard deviations recorded were 5.3 and 4.1 millimeters. The typical value was 1.7 and the lowest value was 0.8 millimeters. Thus, using the typical value of standard deviation and an expected service corrosion rate of five millimeters per year, at a 95% confidence level an expected range for the time for corrosion fuses to leak may be calculated. For a large population of air tanks it may be expected that a range of the time-to-leak is approximately two years.

The variation in corrosion for a given corrosion fuse may be a reflection of corrosion conditions and material variations. The range of diameter values in a single fuse varied from as high as 17 millimeters to as low as 1 millimeter over the two and a half inch length of corrosion fuse that was in the solution. Typical values for diameter variation were around 10 millimeters, but the variation may be related to individual test, i.e., all four corrosion fuses in a given air tank seemed to have similar variations of diameter along their length. The largest corrosion rates (smallest diameters) for a single corrosion fuse were used for all comparisons unless otherwise noted.

Comparison of the fuse corrosion with that of the air tank is also complicated by non-uniform corrosion rates of the air tank. The degree of localized corrosion and the apparent cause will be discussed later. The general metal loss in each air tank was measured and recorded.

Table 2 lists the metal loss for general corrosion for the corrosion fuse and the air tank.

MEASURED METAL LOSS DURING CORROSION
Metal Loss (millimeters)

| Tank | Fuse | Tank | Tank Burst Pressure (PSI) |
|---|---|---|---|
| 1/1 | 25 | 9 (10)** | 950 |
| 1/2 | 25 | 22 | 800 |
| 1/3 | 25 | 48 | no test |
| 1/4 | 25 | 23 | 1,100 |
| 1/5 | 25 | 16 (10)** | 1,050 |
| 1/6 | 26 | 50 (4)** | 800+ |
| 2/1 | 30 | 21 | 800 |
| 2/2 | 18 | 12 | 900+ |
| 2/3 | 15 | 17 | 900 |
| 2/4 | 28 | 7 | 1050 |
| 2/5 | 33+ | 54 (99)** | no test |
| 2/6 | 23 | 25 (65)** | 300 |
| 1/4* | 8 | 10 | |
| 1/4* | 3 | 4 | |

*Tested for three days only
**Tank end cap
+Only two corrosion fuses used, tank corroded in the upside down position Averaging all metal loss measurements for the corrosion fuses and air tanks revealed that, on average, the corrosion rate was virtually the same for the corrosion fuse and the air tank. However, as may be seen in Table 2 above, when evaluating an individual air tank the corrosion rate or amount of metal loss for a given time varied by as much as a factor of two for some air tank and corrosion fuse combinations and varied by a maximum of a factor of four for one test. It is noted that conditions were not optimum for several tests, e.g., some corrosion fuses had solder metal at one end that may have accelerated corrosion of the corrosion fuse far away from the end and different acid solutions appeared to cause localized corrosion in an unusual manner that may not be the case for corrosion by condensate.

In each of the cases where pitting and highly localized corrosion was severe, the metal loss of the air tank was around fifty (50) millimeters and the air tanks were unable to be pressure tested. In one air tank, upon which pressure testing was able to be performed, the burst pressure for the air tank with fifty (50) millimeters of metal loss was over eight hundred (800) PSI. Except for only one test, all hydrostatically tested air tanks had a burst pressure of eight hundred (800) PSI or greater after the corrosion fuse leaked. In an air tank that failed below eight hundred (800) PSI (air tank 2/6 of Table 2), a very high concentration of sulfuric acid was used and the corrosion rate was much higher (two and a half times higher) in the end cap than it was in the cylinder (or shell) of the air tank or the corrosion fuse. It is likely that this type of non-uniform corrosion may not be characteristic of corrosion of moisture condensate, but may be more typical of acid corrosion.

Figure 28:
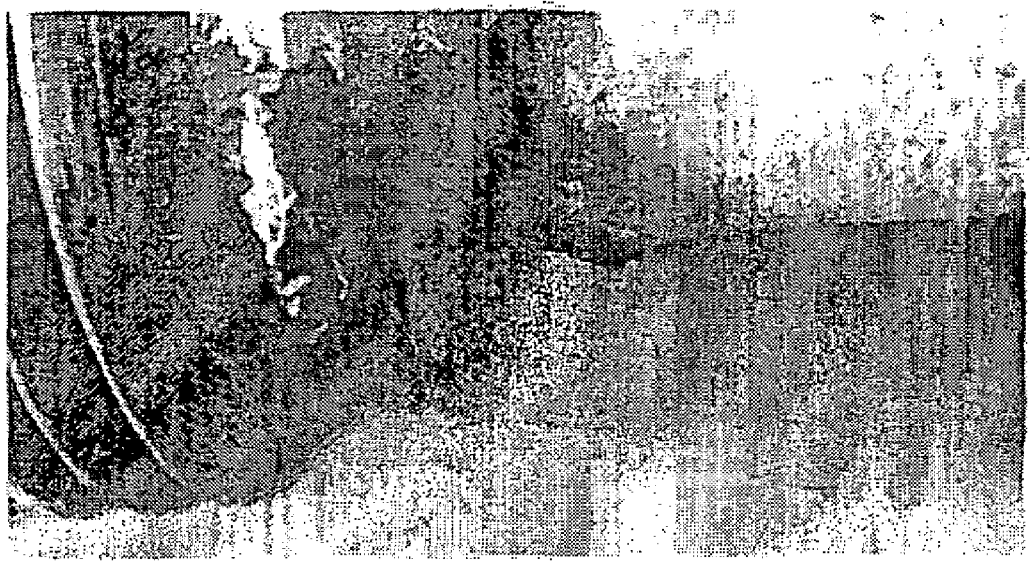
FIG. 28 is a corrosion fuse where a soldering technique was employed to couple the corrosion detector with the plug and further illustrates the corrosion that occurred at the solder area of the corrosion fuse after corrosion has occurred.

3. Fuse to Fitting Joint: The end conditions of the corrosion fuse greatly influenced the corrosion in the immediate area. Several corrosion fuses leaked with only slight general corrosion to the corrosion fuse. In these corrosion fuses, localized corrosion occurred next to the silver solder in the corrosion fuses, see FIG. 28. This was probably a galvanic corrosion effect because the silver solder is more corrosion resistant than the steel. This problem was noted early in the testing program and was circumvented by coating the solder with lacquer. In an attempt to avoid this localized corrosion, a new batch of corrosion fuses was manufactured by fusion welding the tube to the end fitting.

Figure 29:
FIG. 29 is a corrosion fuse where a welding technique was employed to couple the corrosion detector with the plug and further illustrates the corrosion that occurred at the weld joint after the corrosion fuse had been subjected to a corrosive media and corrosion had occurred.

A similar problem occurred with the welded fuses, as shown in FIG. 29. The localized corrosion was severe with one corrosion fuse leaking through the tube wall next to the weld in only two days. For a welded connection, localized corrosion occurred in the tube next to the weld and large pits formed in the weld metal. Because this mode of corrosion fuse failure was considered premature, corrosion fuses of this design were also coated with lacquer at the weld.

Figure 30:
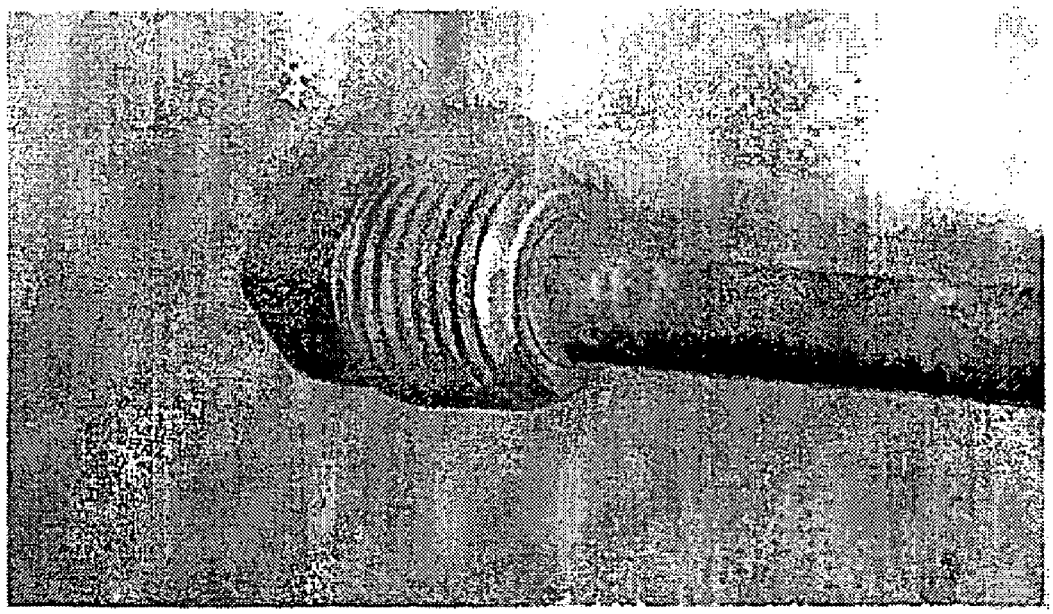
FIG. 30 illustrates a press-fit joint between a corrosion detector (tube) and a plug employing a bonding agent.
Figure 31:
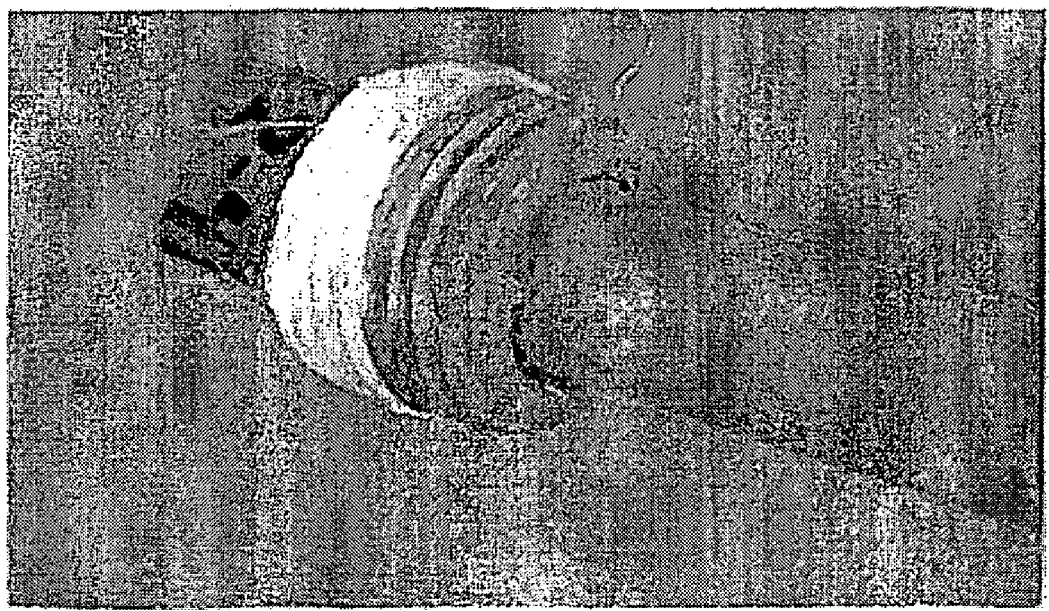
FIG. 31 illustrates the same press-fit joint of FIG. 30 after being subjected to a corrosive media.

A third attempt was made to have a tube-to-fitting joint that did not preferentially corrode. This approach was to make a press fit between the tube and the fitting. A polymer-bonding agent was applied to insure a hermetic seal. The corrosion fuse of the present invention may employ polymer-binding agents, which may have various compositional characteristics and functional capabilities. For instance, the agent may provide a seal which excludes air and/or moisture. Further, the agent may have changing properties during use. For example, the agent may originally start in one form (i.e., liquid) and during application and use turn into a secondary form (i.e., solid). Other types of agents, with various properties and characteristics, as contemplated by those of ordinary skill in the art may be employed without departing from the scope and spirit of the present invention. FIG. 30 shows a new joint and FIG. 31 shows a joint after only twelve (12) millimeters of metal loss over most of the corrosion fuse. For the other two joining methods, localized corrosion occurred in each corrosion fuse. For the press-fit joint, some of the joints did not appear to have significant localized attack. Examination of several fuses during the corrosion test revealed an apparent localized corrosion associated with an incomplete bond between the polymer and the tube or a gap between the tube and the fitting. These gaps caused accelerated corrosion known as crevice corrosion. Because this localized corrosion was also considered abnormal, this corrosion fuse design was also coated with lacquer at the joint to assist in preventing premature leaks.

Figure 32:
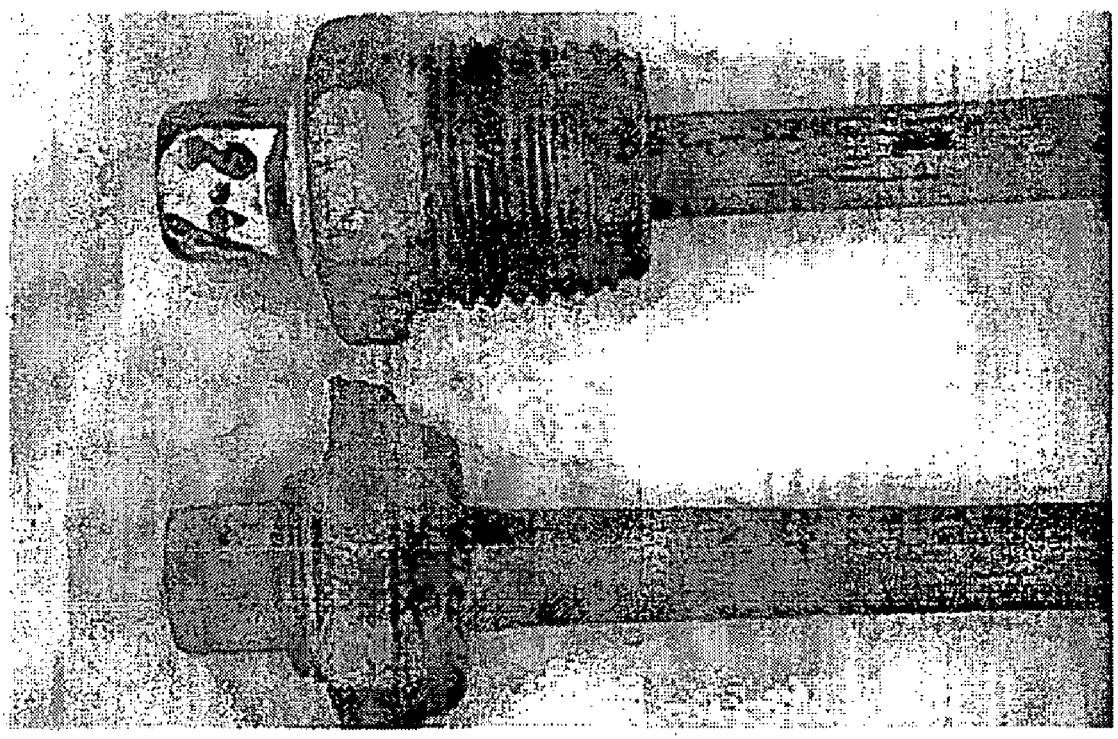
FIG. 32 illustrates a first corrosion detector coupled with a first galvanized steel plug (top) and a second corrosion detector coupled with a second cast iron plug (bottom) after both the first and second corrosion detectors and plugs had been subjected to a corrosive media.

Perhaps the most dramatic demonstration of the effect of different materials on corrosion occurred when tubes were inserted inside a bushing. This was done for two tanks that were turned upside down for testing. One tank had a galvanized bushing and the other had a cast iron bushing. The cast iron bushing was corroded away and the tube was protected in the area surrounded by the bushing, as shown in FIG. 32.

Figure 33:
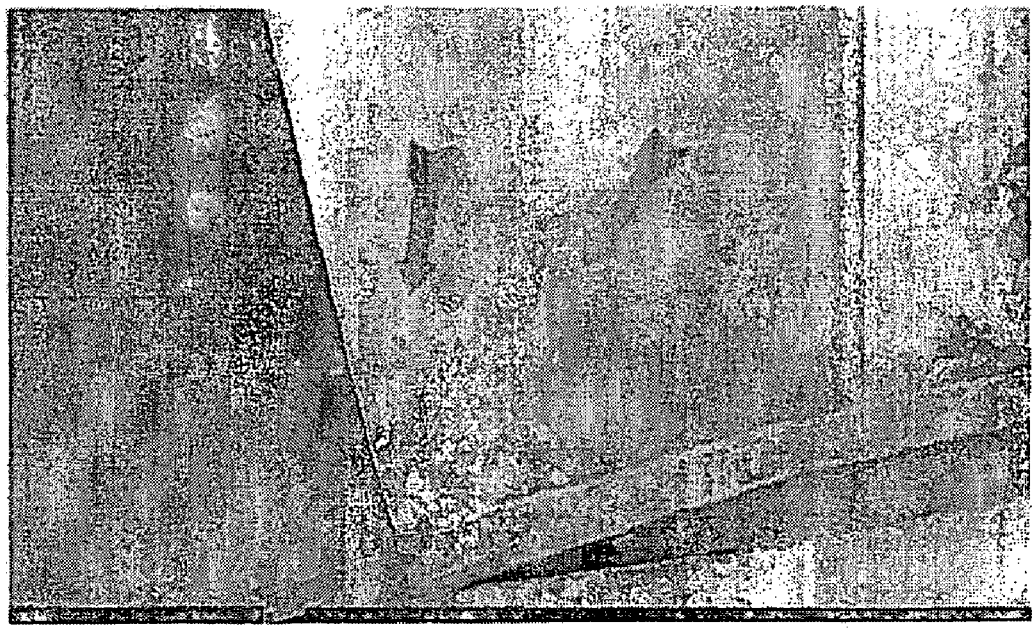
FIG. 33 illustrates the inside of a burst air tank where the two top arrows indicate the localized corrosion inside an air tank at an external weld for a wheel bracket and a bottom arrow indicates that the burst fracture of the air tank followed the thinner wall area associated with the localized corrosion of the heat-affected-zone (HAZ) in the seam weld.
Figure 34:
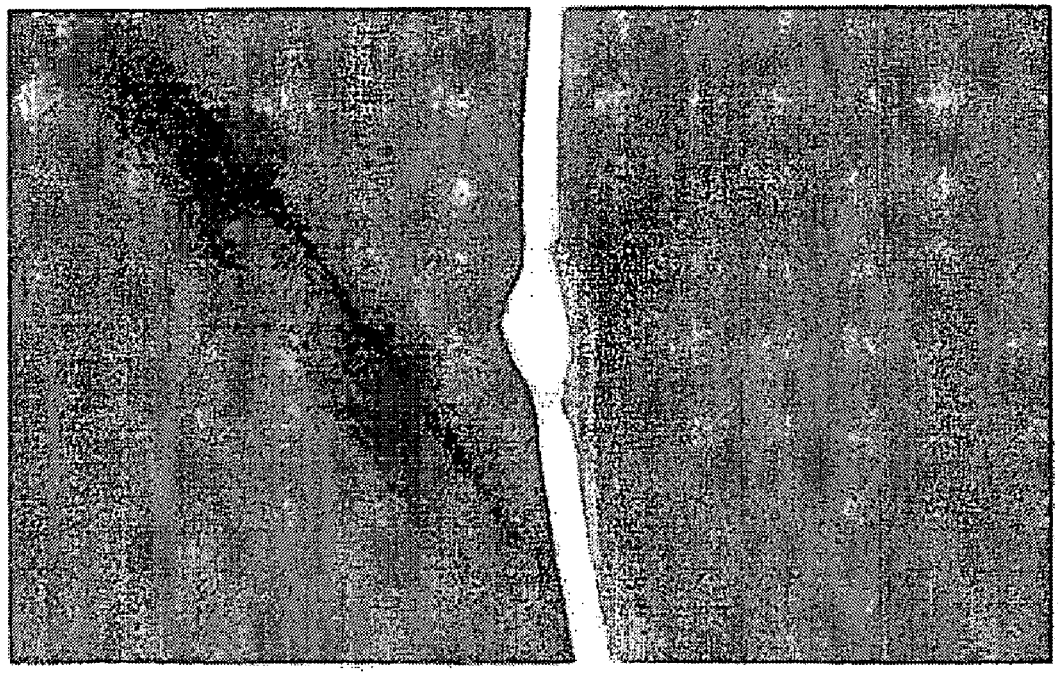
FIG. 34 is a cross-section view illustrating a corroded air tank at a submerged seam weld.

4. Tank Burst Location: The burst location of tanks was often associated with localized corrosion attack. When the horizontal seam welds were below the waterline there was always localized corrosion in the heat-affected zone (HAZ). This was not only the case for seam welds but exterior welds connecting wheel brackets resulted in a HAZ that was exposed to the acid solution. FIG. 33 shows the localized corrosion inside the tank at an external weld for a wheel bracket and it shows that the burst fracture of a tank followed the thinner wall area associated with localized corrosion of the HAZ in the seam weld. FIG. 34 shows an end view of a weld under the solution and the local metal thinning at the HAZ that is on both sides of a weld.

Figure 35:
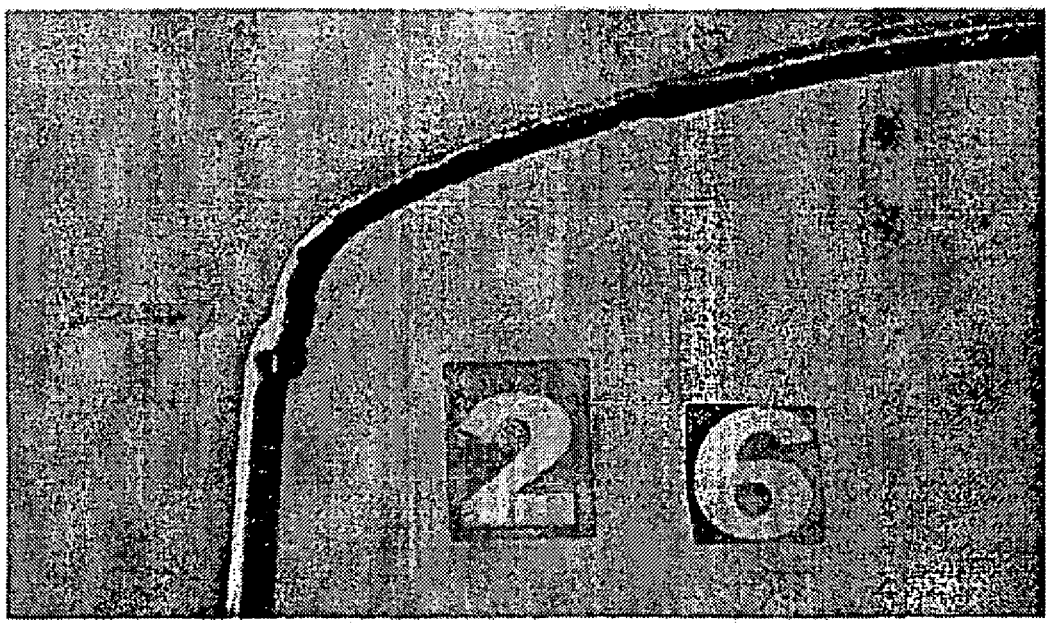
FIG. 35 is a cross-section view illustrating the different corrosion characteristics observed between portions of a cylinder body and an end cap of a compressed air tank upon being subjected to a corrosive media.

Higher corrosion rates at the waterline are common for aqueous corrosion. This type of localized corrosion occurred in some of the tanks, but it was not consistent for all solutions and even appeared to vary from compressed air tank to compressed air tank for the same solution concentration. This type of localized corrosion is most severe when the waterline is constant throughout the test time. In several tests that showed a tendency for waterline attack, the level of solution was not held constant for the entire test. This is because of some slight leaking of corrosion fuses or some slight volume differences when the solution batches were changed. In those cases where the solution level was essentially constant for the entire test period and where waterline attack was active, a deep groove occurred at the waterline. The degree of localized attack at the waterline was only slightly greater than the general corrosion attack, as may be seen in FIG. 35. The waterline did in some cases have a greater density of pits than the rest of the corroded surface area. This is also true of the HAZ which often had pits that were deeper than those found in other areas in contact with the solution.

Localized corrosion at the waterline appears to have led to failure in the burst test (was the weakest area of the tank) for about half of the compressed air tanks. One air tank (1/1 of Table 2) had only lost about nine (9) millimeters of metal thickness due to general corrosion, but had lost about thirty (30) millimeters in some areas of the waterline attack groove. This tank burst at nine hundred fifty (950) PSI which is close to the value one would predict from a metal thickness of seventy (70) millimeters, i.e., 70 millimeters/100 millimeters-980 psi/1,400 PSI (1,400 PSI is the typical burst pressure for a new compressed air tank of the size tested). In another air tank (1/2 of Table 2), one of the corrosion fuses had leaked and a new waterline formed. Failure occurred at this new waterline. It is noted that the corrosion fuse did not exhibit localized attack at the waterline to the same degree or as frequently as did the compressed air tanks. It is not clear if this is because of the geometry difference between the fuse and the air tank or if it is related to any metallurgical difference between the compressed air tank metal and the metal of the fuses. It is possible that in a condensate water environment that the corrosion fuse and compressed air tank may have the same tendency for waterline localized corrosion.

For several of the compressed air tanks (three), the weakest location was the reduced thickness at the HAZ caused by accelerated localized corrosion in this area. In addition, two compressed air tanks could not be burst because there were too many pits in the HAZ that went completely through the tank.

Some of the compressed air tanks failed in the area of general corrosion. For one tank, the fracture appeared to originate in the area of an exterior attachment. The only apparent weakening of the compressed air tank was uniform general corrosion. But during pressure testing, the tank began to deform and the local constraint caused by the attachment lead to a fracture initiation at that location. A similar failure response was seen in a new, un-corroded compressed air tank.

Table 3 lists the location of the failure as it related to the "waterline" or HAZ.

| Burst Location & Degree of Waterline Attack | | |
| --- | --- | --- |
| Tank | Location | Waterline Attack Y/N |
| 1/1 | Waterline | Y 2 levels, some pits |
| 1/2 | Waterline | Y 3 levels, heavy pitting |
| 1/3 | NA (pits) | Y slight |
| 1/4 | General* | Y slight |
| 1/5 | Waterline | Y |
| 1/6 | NA (pits) | N |
| 2/1 | HAZ | Y slight |
| 2/2 | HAZ | N |
| 2/3 | HAZ | Y slight |
| 2/4 | Waterline/weld** | Y slight |
| 2/5 | NA (end cap)+ | Y slight |
| 2/6 | General end cap | Y slight, heaving pitting |

*failure in area of general corrosion
**the waterline and weld were at the same location
+the end cap corroded through Only two compressed air tanks ruptured during the burst test in some area other than these two locations. One failed in an area of general corrosion with the origin related to a constraint of an exterior bracket, while one was in an area of general corrosion that was much more severe in the end cap compared to the cylinder portion of the compressed air tank. This air tank (2/5 of Table 3) was subjected to a more severe, more concentrated acid solution, 1.33M sulfuric acid. This suggests that high acid concentrations corrode differently than low concentrations.

Figure 36:
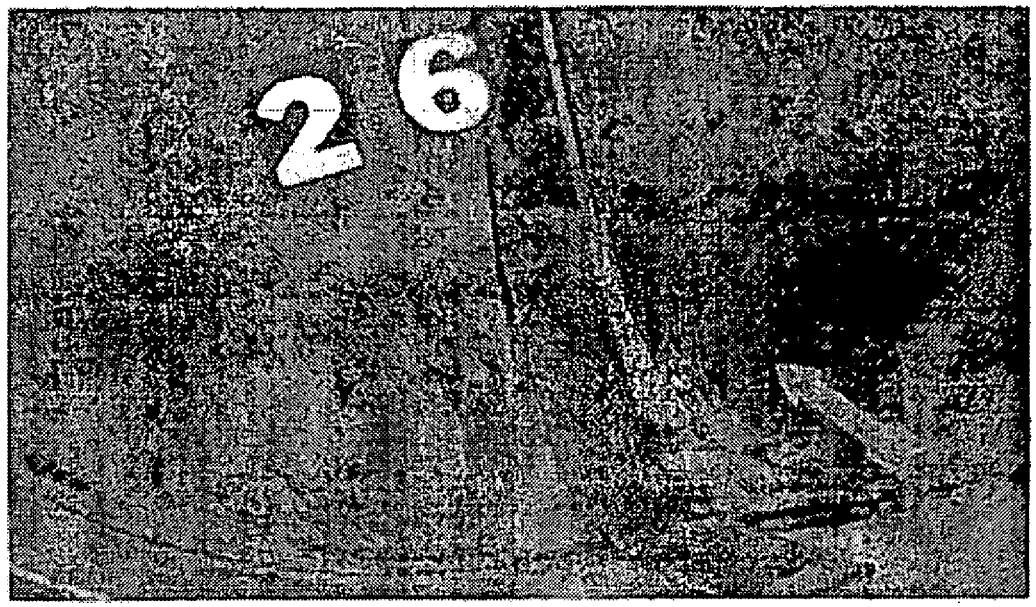
FIG. 36 illustrates the inside surface of an end cap where the arrow is aligned with the corrosion grooves in the end cap.

5. Localized Corrosion: There was no clear trend for local corrosion depending on acid concentration. However, differences appeared between the various compressed air tanks which specified ASTM SA-414 Grade G steel so any difference would be natural variation in material meeting this specification. For some compressed air tanks the corrosion of the end cap was noticeably different than the cylinder body, see Table 2 for compressed air tanks 1/6, 2/5, and 2/6; also see FIG. 36.

Table 4 lists the chemical analysis of the end caps and cylinder portions for a compressed air tank along with the chemical analysis of a corrosion fuse.

| Chemical Analysis of Tank Steel In weight % | | | | | | |
|---|---|---|---|---|---|---|
| | | End Cap | Cylinder | End Cap | Cylinder | Fuse |
| Aluminum | Al | 0.04 | 0.03 | 0.04 | 0.04 | 0.04 |
| Carbon | C | 0.2 | 0.29 | 0.28 | 0.26 | 0.18 |
| Chromium | Cr | 0.03 | 0.03 | 0.03 | 0.009 | 0.09 |
| Copper | Cu | 0.026 | 0.009 | 0.041 | 0.01 | <0.005 |
| Manganese | Mg | 0.78 | 0.86 | 0.8 | 0.97 | 0.38 |
| Molybdenum | Mo | <0.005 | <0.005 | <0.005 | <0.005 | <0.005 |
| Nickel | Ni | 0.01 | 0.01 | 0.02 | 0.01 | 0.008 |
| Phosphorous | P | 0.01 | 0.007 | 0.009 | 0.007 | 0.007 |
| Silicon | Is | <0.005 | <0.005 | <0.005 | <0.005 | <0.005 |
| Sulfur | S | 0.01 | 0.005 | 0.006 | 0.01 | 0.009 |
| Titanium | Ti | <0.005 | <0.005 | <0.005 | <0.005 | <0.005 |
| Vanadium | V | <0.005 | <0.005 | <0.005 | <0.005 | <0.005 |

As may be seen from Table 4, there were no significant chemical differences among the air tank materials. Likewise, the metallurgical microstructure was virtually the same for the tanks. Particular attention was paid to the amount and size of manganese sulfide stringers. There was no discernable difference for all samples examined. Thus, there was no apparent metallurgical reason for large variations in corrosion rate within a given tank and among the various compressed air tanks.

Pitting seemed to be slight for the general area of the compressed air tank subjected to acid solution. However, weld metal had a tendency to pit severely. In some cases, the HAZ and waterline contained very deep pits. This severe pitting did not seem to follow a general trend and was not severe for some of the compressed air tanks.

In some compressed air tanks and often in the corrosion fuse, elongated pits, or short grooves would form. These were very narrow and their depth could not be accurately measured with the pointed micrometer. Their directionality, especially in the end caps, suggested that they were related to the anisotropy of the forming process used to fabricate the wrought material. That is, the highly localized attack may be related to the manganese sulfide stringers normally formed in steel of the general quality of ASTM SA-414.

Figure 37:
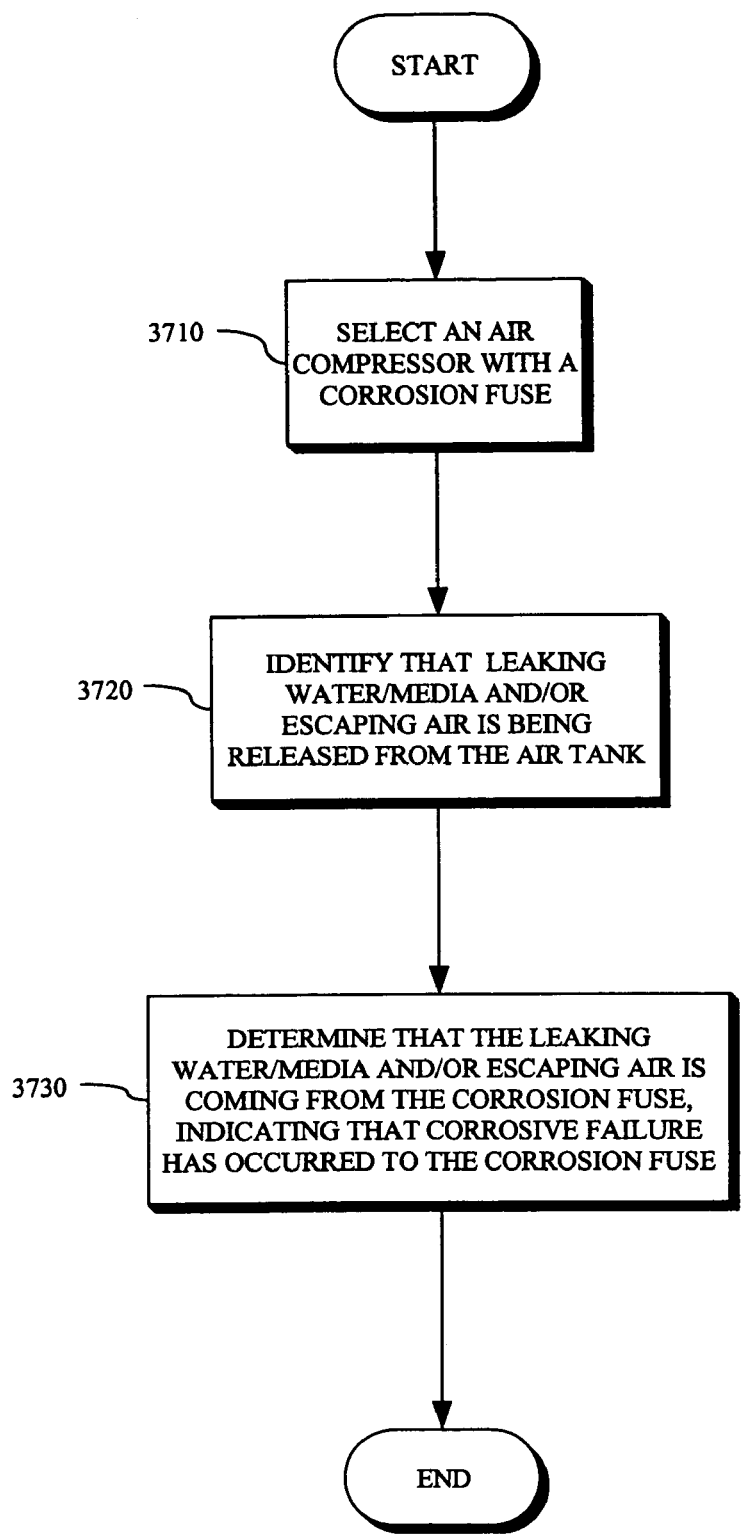
FIG. 37 is a block diagram illustrating a method for detecting the internal corrosive failure rate of a compressed air tank.

It is understood that the corrosion fuse of the present invention, as shown in FIG. 37, establishes a method of identifying the corrosive failure of a compressed air tank, which may be more effective than previous devices, such as the "telltale hole" described previously. In step 3710 a user of the present invention selects a compressed air tank which employs a corrosion fuse. Typically, the user may be selecting the compressed air tank as part of a mechanical assembly, such as an air compressor. Next, in step 3720, the user of the compressed air tank employing the corrosion fuse either identifies a leaking of substances, such as water and/or other media, from the compressed air tank or identifies an escaping of compressed air from the air tank. In either circumstance the user in step 3730 determines that that the leaking water/media or escaping air is coming through the corrosion fuse. This indicates to the user that corrosive failure has occurred to the corrosion fuse. The corrosive failure of the corrosion fuse provides the indication to the user that the compressed air tank has experienced corrosive damage which may eventually lead to a failure of containment capabilities by the compressed air tank. The user may then decide to discontinue use of the air compressor assembly containing a failed corrosion fuse.

In a further step of the present invention, the user may identify alternative visual indicators which provide the determination that corrosive failure has occurred to the corrosion fuse. For example, the user may identify an expanding rubber diaphragm extending from the corrosion fuse. The user may identify a colored water and/or media leaking from the corrosion fuse. In addition, the user may identify a light emitting diode from a display device of a visual sensor assembly which indicates corrosive failure has occurred to the corrosion fuse. The identification of corrosive failure may be ascertainable through an audible indicator. For example, the escaping gas may cause a whistling noise which the user may identify as the indication that corrosive failure has occurred to the corrosion fuse.

Figure 38A:
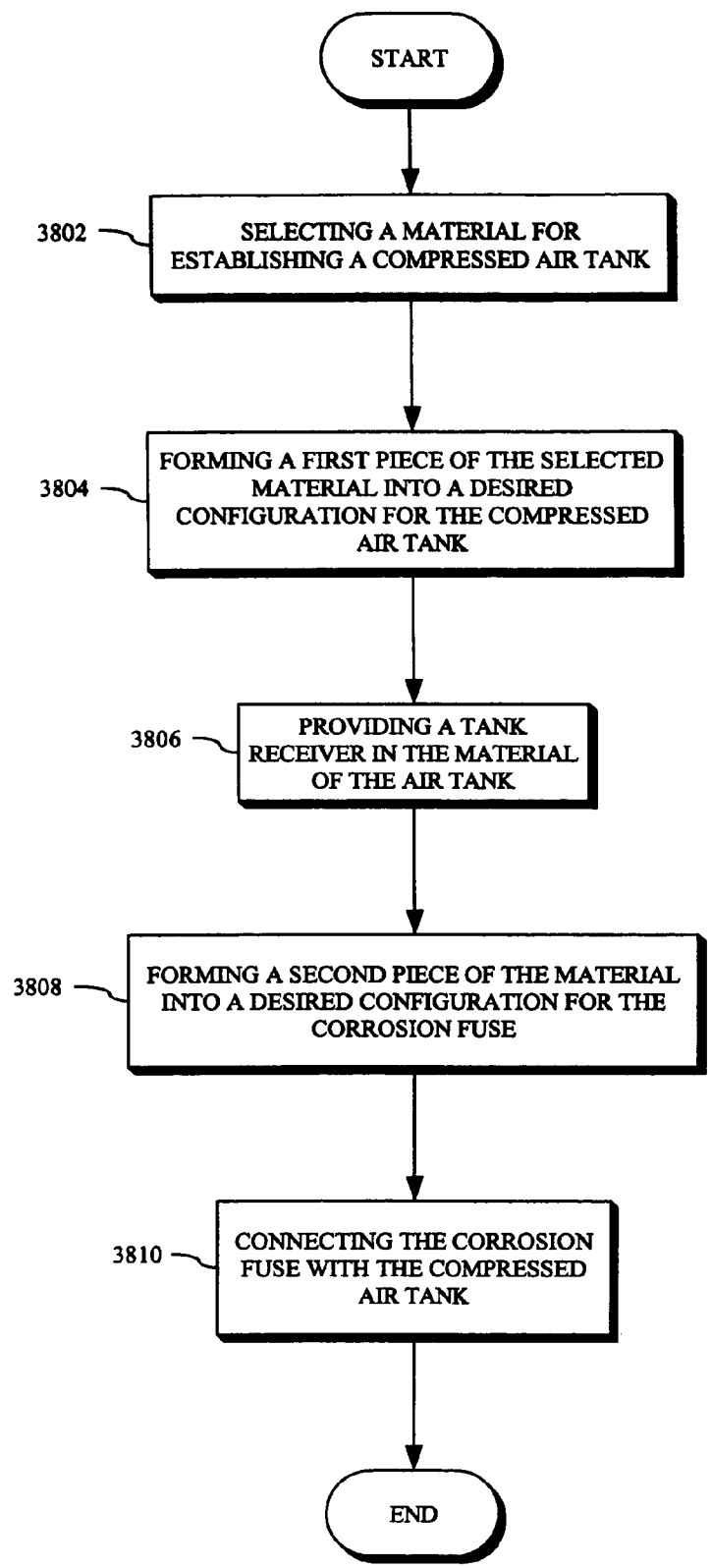
FIG. 38A is a block diagram illustrating a method of manufacturing a compressed air tank.

A method of manufacturing a compressed air tank is shown in FIG. 38A. In a first step 3802 a material is selected for constructing the compressed air tank. As previously described, the material selected may vary from steel (alloys), to alternative metals, to composites. From a first piece of the selected material the compressed air tank is formed in step 3804. The manufacturer may determine the dimensional characteristics of the compressed air tank which may affect the preparation of the first piece of material from which the air tank is formed. In step 3806 a tank receiver is formed into the compressed air tank. From a second piece of the selected material a corrosion fuse is formed in step 3808. Similar to the preparation of the air tank, the preparation of the piece of material for constructing the corrosion fuse may be determined by the dimensional characteristics established by the manufacturer for the forming of the corrosion fuse. It is to be understood that the forming of the material may be accomplished through the utilization of various manufacturing techniques and processes as may be contemplated by those of ordinary skill in the relevant art. For example, the forming of the corrosion fuse may be accomplished through a standard cutting process, stamping process, or molding process. Still further, the process employed may be enabled to provide various configurations from a single run of material. For example, the process may alternate between the manufacture of a generally cylindrical corrosion fuse and a generally star-shaped corrosion fuse. After their formation the compressed air tank and the corrosion fuse are connected, via the tank receiver, in step 3810. The connection may occur utilizing various connection techniques, such as welding, brazing, soldering processes, connecting mechanisms, such as a compression lock mechanism, snap fit mechanism, friction fit mechanism, latch lock mechanism, spring loaded lock mechanism, and/or various adhesives, such as organic adhesives. Further, any of these techniques, mechanisms, and adhesives may be employed alone or in various combinations with one another.

The method of manufacturing a compressed air tank may further include connecting a visual or audible indicator to the corrosion fuse. This may promote the ease with which the user of the present invention identifies a leak indicating a corrosive failure of the corrosion fuse. It is contemplated that the tamper resistant features identified previously may be included as separate steps in the manufacturing process. For example, the first and second inner diameters of the plug may be offset in a step of the manufacturing process in order to assist in preventing the improper use of the present invention.

Figure 38B:
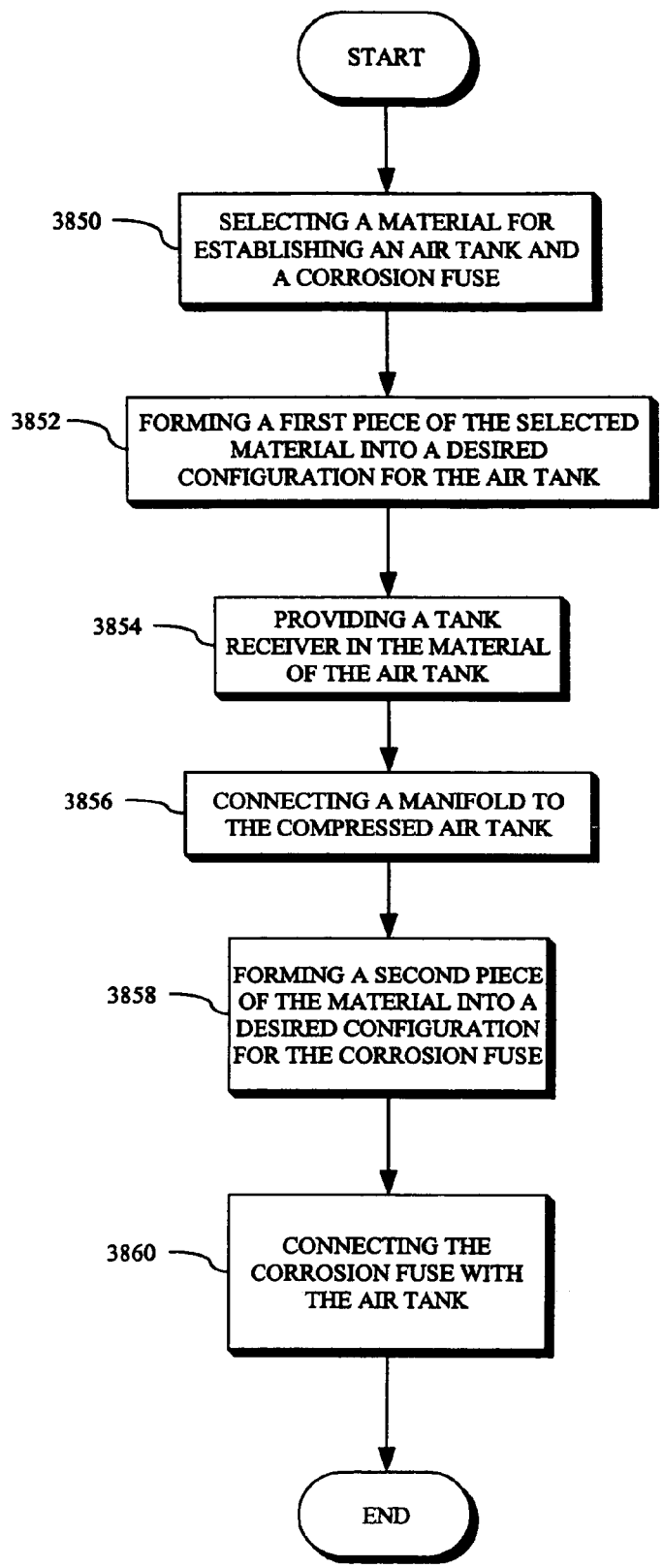
FIG. 38B is a block diagram illustrating a method of manufacturing an air compressor assembly including a corrosion fuse.

In a further alternative embodiment shown in FIG. 38B, a method of manufacturing an air compressor assembly including a corrosion fuse is provided. In a first step 3850 a material is selected for constructing a compressed air tank and a corrosion fuse. The material selected is used for both the compressed air tank and corrosion fuse to promote a similar corrosive rate of the compressed air tank and corrosion fuse. The compressed air tank is provided for the storage of media at elevated pressure. In a preferred embodiment, the compressed air tank may be established as a horizontal air tank portable air compressor assembly including a horizontal air tank connected with a motor and manifold and further including a wheel assembly for portability. In an alternative embodiment, the compressed air tank may be established as a vertical air tank portable air compressor assembly or as a stationary air tank either horizontal or vertical.

In step 3852 of the method of manufacture, a first piece of the material is formed into the desired configuration for the compressed air tank. Following the formation of the compressed air tank, in step 3854 a tank receiver is provided in a location upon the compressed air tank which promotes the usefulness of the tank receiver for assisting in the identification of corrosive failure. In step 3856 a manifold is connected with the compressed air tank. The manifold allows a user access to and control over the flow of compressed air which may be stored in the compressed air tank. In step 3858 the corrosion fuse is formed into a desired configuration using a second piece of the selected material. Similar to the formation possibilities as described above, the corrosion fuse may be manufactured through the utilization of a variety of manufacturing processes and techniques. The corrosion fuse is then connected with the compressed air tank in step 3860 by inserting a corrosion detector, of the corrosion fuse, through the tank receiver and within the interior of the compressed air tank to provide an indicator for corrosive effects occurring within the compressed air tank. The corrosion fuse may employ a flange, which is connected with the compressed air tank in a position aligning it with the tank receiver. The flange aligns a dual inner diameter configuration with the tank receiver. A corrosion detector is connected on one end with a plug and the corrosion detector has an opposite end which is sealed. The corrosion detector and the plug are inserted into and through the dual inner diameter configuration of the flange. The corrosion detector inserts through the flange and tank receiver extending into the interior of the compressed air tank. The plug is secured in its position within the dual inner diameter configuration of the flange, thereby establishing an air compressor assembly including a corrosion fuse.

The method of manufacturing an air compressor assembly may further include steps for connecting a visual or audible indicator to the corrosion fuse. This may promote the ease with which the user of the present invention identifies a leak indicating a corrosive failure of the corrosion fuse. It is contemplated that the tamper resistant features identified previously may be included as separate steps in the manufacturing process. For example, the first and second inner diameters of the plug may be offset in a step of the manufacturing process in order to assist in preventing the improper use of the present invention.

Figure 39:
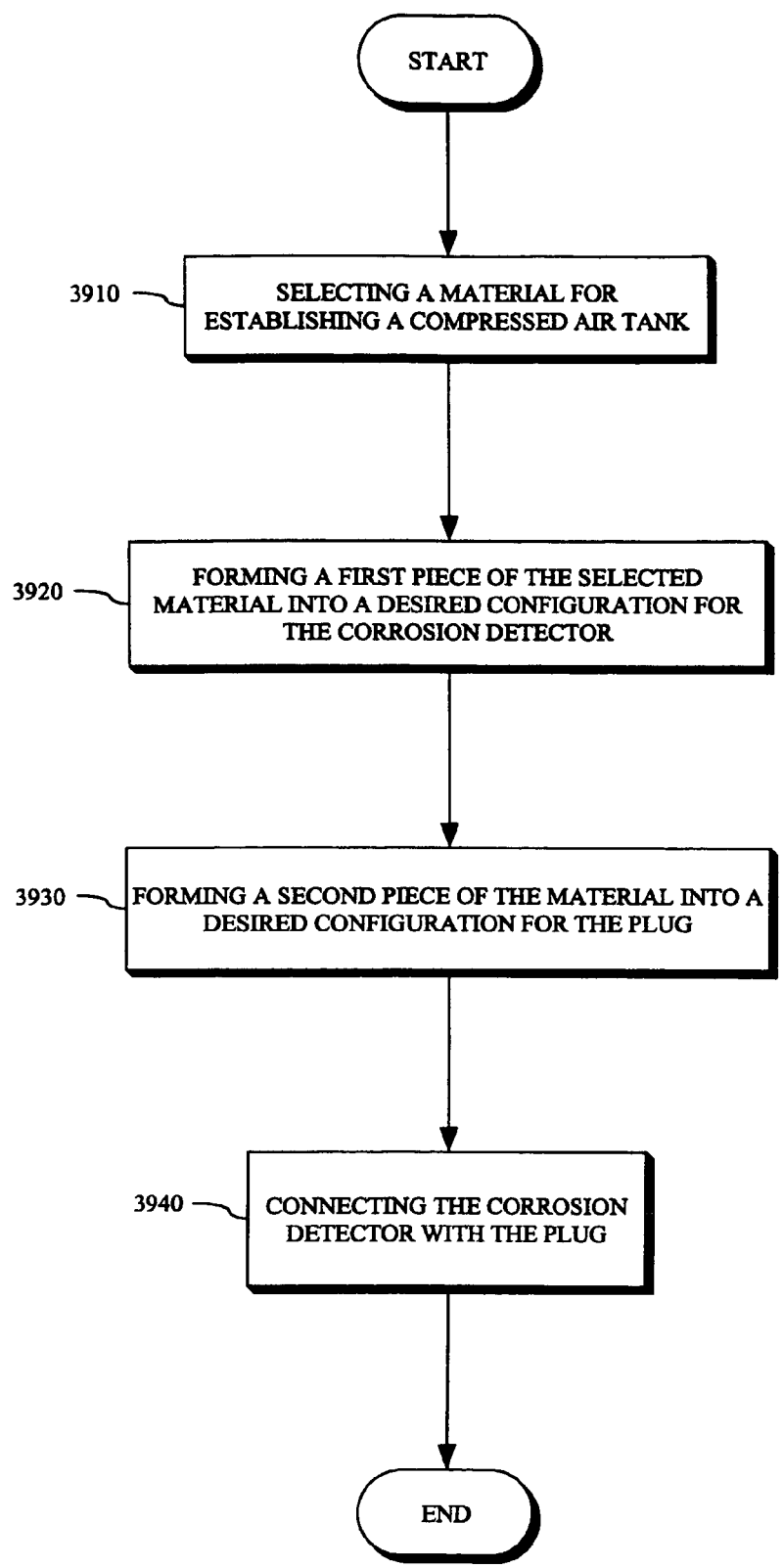
FIG. 39 is a block diagram illustrating a method of manufacturing a corrosion fuse in accordance with an exemplary embodiment of the present invention.

Referring now to FIG. 39, a method 3900 for the manufacture of a corrosion fuse for a compressed air tank in accordance with an exemplary embodiment of the present invention is shown. A first step 3910 is material selection. The material selected may be of a steel alloy, various other metals, or a composite material, and the like, which provide sufficient structural strength and corrosive characteristics. The corrosive characteristics of the material selected for the corrosion fuse may be similar to the corrosive characteristics of the compressed air tank to which the corrosion fuse connects. Alternatively, the material selected may have different corrosive characteristics than that of the compressed air tank. In step 3920, the first piece of selected material is formed into a corrosion detector. In a preferred embodiment, the corrosion detector is constructed as a tube which is sealed on one end and open to the environment on the other end. The corrosion detector, formed from the first piece of material, may be variously constructed and configured as described previously in reference to corrosion detector 212. It is to be understood that the forming of the material may be accomplished through the utilization of various manufacturing techniques and processes as may be contemplated by those of ordinary skill in the relevant art. For example, the forming of the corrosion detector may be accomplished through a standard cutting process, stamping process, or molding process. Still further, the process employed may be enabled to provide various configurations from a single run of material. For example, the process may alternate between the manufacture of a generally cylindrical corrosion detector and a generally star-shaped corrosion detector.

The second piece of the selected material is formed into a plug in step 3930. The plug formed form the second piece being variously constructed and configured as described previously in reference to plug 208. After the forming of the corrosion detector and the plug, in step 3940 the corrosion detector is connected with the plug. The joining of the corrosion detector and the plug may be accomplished utilizing various techniques, such as various welding, soldering, and brazing techniques, by utilizing various mechanical connection systems, such as compression lock systems, friction fit system, snap-fit systems, or by utilizing adhesives, such as wicking cement, organic adhesives, and the like, which provide the advantageous characteristic of keeping moisture and air out of the joint. Alternative joint construction applications, as contemplated by those of ordinary skill in the art may be utilized without departing from the scope and spirit of the present invention. It is contemplated that the various joint construction applications described above may be used alone or in various combinations with one another.

The forming of the first piece of the selected material into the corrosion detector may further include the step of selecting a desired configuration for the corrosion detector and then forming the corrosion detector into that desired configuration. For example, in a preferred embodiment, the corrosion detector 212 is shown as a generally cylindrical tube. However, the present method of manufacture enables the manufacturer to select various other configurations, such as those shown in FIGS. 14 through 18, and provide the corrosion detector in that configuration.

In an additional step of the method 3900, a crimped and sealed first end of the corrosion detector is formed. The crimped and sealed first end may be similar to that shown in FIG. 12 and described in reference thereto above. It is further contemplated that the method may include the provision of three pieces of the selected material. Then in additional forming step, a cap is formed from the third piece of the selected material. The cap may be variously constructed and configured in a manner similar to that described above in reference to cap 216 and shown in FIGS. 8 through 11. After the formation of the corrosion detector, plug, and cap, all three items are then connected together. One end of the corrosion detector connects with the plug while the opposite end connects with the cap. The joining of the cap may occur utilizing various techniques, technologies, and the like, which provide the corrosive characteristics desired as described above in reference to FIGS. 8 through 12 and also may be similar to those joining applications described in reference to the joining of the plug with the corrosion detector.

It will be appreciated by those of skill in the relevant art that the corrosion fuse 200, and its numerous implementations described in the various embodiments throughout the instant application, is capable of being retro-fitted with existing compressed air tanks and into assemblies employing these air tanks. The retrofitting is enabled by the novel design of the present invention, whereby, the connection of the corrosion fuse with the compressed air tank does not necessarily require compliance with ASME code. This increases the ease with which retro-fitting may occur.

As previously described the corrosion fuse of the present invention may be variously configured and constructed with walls of varying thickness. This may provide another advantage in the retro-fitting capability in that users of existing compressed air tanks may be able to retro-fit corrosion fuses with varying wall thickness. This variation may allow the corrosion fuses to experience corrosive failure at an increased or decreased rate depending on the wall thickness. It is to be understood that a method of retro-fitting a corrosion fuse with a compressed air tank is contemplated by the present invention. The method including the steps of selecting a corrosion fuse assembly. The corrosion fuse assembly including a flange, plug, and corrosion detector. The selection being based upon a desired wall thickness of the corrosion fuse. The desired wall thickness providing a predictive indication of corrosive failure possibly within a pre-set period of time. In a next step the user may bore a hole through the wall of a compressed air tank, locating the bore generally at a lowest gravitational point of the compressed air tank. The size of the bore corresponding to the size of the corrosion detector of the corrosion fuse assembly selected. The user may then connect the flange to the outer wall of the compressed air tank in a position about the hole through the wall of the compressed air tank. The user then connects the plug with a second "open" end of the corrosion detector. After the plug and corrosion detector are connected the user may then insert the corrosion detector, beginning with a first end of the corrosion detector, through the hole in the wall of the compressed air tank. Before the corrosion detector is fully extended into the compressed air tank, the plug engages with the flange. Upon this engagement the user connects the plug with the flange. When the plug is fully connected with the flange the corrosion detector is fully extended into its proper position within the compressed air tank. It is understood that the position of the flange is determined by the position of the plug when the corrosion detector is extended through the hole.

The retro-fitting process may further include steps for connecting an indication system to the corrosion fuse assembly. This may promote the ease with which the user of the present invention identifies a leak indicating a corrosive failure of the corrosion fuse. It is contemplated that the tamper resistant features identified throughout the instant application may be included as separate steps in the retrofitting process. For example, the plug may be offset from the centerline of the corrosion detector in order to assist in preventing the improper use of the present invention.

It is understood that the specific order or hierarchy of steps in the methods disclosed are examples of exemplary approaches. Based upon design preferences, it is understood that the specific order or hierarchy of steps in the method can be rearranged while remaining within the scope and spirit of the present invention. The accompanying method claims present elements of the various steps in a sample order, and are not necessarily meant to be limited to the specific order or hierarchy presented.

It is believed that the present invention and many of its attendant advantages will be understood by the forgoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof. It is the intention of the following claims to encompass and include such changes.

What is claimed is:

1. A corrosion fuse for use in a compressed air tank formed of a corrodible material, the corrosion fuse comprising:
   a corrosion detector formed of substantially the same corrodible material as that of the compressed air tank, the corrosion detector mounted through a wall of the compressed air tank for storing air at an elevated pressure and extending substantially into an interior of the compressed air tank,
   wherein the corrosion detector provides a predictive indication of a pre-determined amount of corrosion occurring generally at a waterline.

2. The corrosion fuse of claim 1, wherein the predictive indication is correlated to a pre-determined amount of corrosion having occurred to the compressed air tank.

3. The corrosion fuse of claim 1, wherein the corrosion detector defines a recess which is configured to be exposed to an environment outside the compressed air tank.

4. The corrosion fuse of claim 1, further comprising a plug which connects with the corrosion detector.

5. The corrosion fuse of claim 4, further comprising a flange which connects with the compressed air tank and the plug.

6. The corrosion fuse of claim 1, further comprising an indication system which is at least one of a visual indication system and an audible indication system.

7. The corrosion fuse of claim 1, further comprising at least one tamper resistant feature.

8. A corrosion fuse for use in a compressed air tank formed of a corrodible material, the corrosion fuse comprising:
   a plug;
   a corrosion detector formed of substantially the same corrodible material as that of the compressed air tank, and connected to the plug, the corrosion detector extending substantially into an interior of the compressed air tank for storing air at an elevated pressure;
   wherein the corrosion detector provides a predictive indication of a pre-determined amount of corrosion occurring generally at a waterline.

9. The corrosion fuse of claim 8, wherein the predictive indication is correlated to a pre-determined amount of corrosion having occurred to the compressed air tank.

10. The corrosion fuse of claim 8, wherein the corrosion detector defines a recess which is configured to be exposed to an environment outside the compressed air tank.

11. The corrosion fuse of claim 8, further comprising a flange which connects with the compressed air tank and the plug.

12. The corrosion fuse of claim 8, further comprising an indication system which is at least one of a visual indication system and an audible indication system.

13. The corrosion fuse of claim 8, further comprising at least one tamper resistant feature.

14. A corrosion fuse for use in a compressed air tank, comprising:
   a compressed air tank formed of a corrodible material, the compressed air tank for storing air at an elevated pressure; and
   a corrosion detector formed of substantially the same corrodible material as that of the compressed air tank, the corrosion detector mounted through a wall of the compressed air tank and extending substantially into an interior of the compressed air tank;
   wherein the corrosion detector provides a predictive indication of a pre-determined amount of corrosion having occurred generally at a waterline inside the compressed air tank.

15. The corrosion fuse of claim 14, wherein the position of the corrosion detector in the compressed air tank corresponds to a lowest gravitational point in the compressed air tank.

16. The corrosion fuse of claim 14, further comprising a plug connected to the corrosion detector.

17. The corrosion fuse of claim 16, further comprising a flange connected to the compressed air tank, the flange being connected with the plug connected to the corrosion detector.

18. The corrosion fuse of claim 14, further comprising an indication system including at least one of a visual indication system and an audible indication system.

19. The corrosion fuse of claim 14, further comprising at least one tamper resistant feature.

* * * * *